US011439680B2

United States Patent
Campos et al.

(10) Patent No.: US 11,439,680 B2
(45) Date of Patent: Sep. 13, 2022

(54) **VETERINARY COMPOSITION OF MARINE ALGAE AND *ANDROGRAPHIS* SP EXTRACTS, WHICH CAN BE USED TO TREAT INFECTIONS IN FISH**

(71) Applicant: MAQUI NEW LIFE S.A., Santiago (CL)

(72) Inventors: Paula Miranda Campos, Puerto Montt (CL); Claudio Rabuco Jeraldino, Santiago (CL)

( * ) Notice: Subject to any disclaimer, the term of this patent is extended or adjusted under 35 U.S.C. 154(b) by 502 days.

(21) Appl. No.: 15/565,091

(22) PCT Filed: Apr. 6, 2016

(86) PCT No.: PCT/CL2016/050015
§ 371 (c)(1),
(2) Date: Oct. 6, 2017

(87) PCT Pub. No.: WO2016/161534
PCT Pub. Date: Oct. 13, 2016

(65) Prior Publication Data
US 2018/0289759 A1    Oct. 11, 2018

(30) Foreign Application Priority Data
Apr. 8, 2015 (CL) .................................... 876-2015

(51) Int. Cl.
| | | |
|---|---|---|
| *A61K 36/53* | (2006.01) | |
| *A61K 36/03* | (2006.01) | |
| *A23K 50/80* | (2016.01) | |
| *A61K 36/19* | (2006.01) | |
| *A23K 20/163* | (2016.01) | |
| *A61P 31/12* | (2006.01) | |
| *A61P 31/04* | (2006.01) | |

(52) U.S. Cl.
CPC ............ *A61K 36/53* (2013.01); *A23K 20/163* (2016.05); *A23K 50/80* (2016.05); *A61K 36/03* (2013.01); *A61K 36/19* (2013.01); *A61P 31/04* (2018.01); *A61P 31/12* (2018.01)

(58) Field of Classification Search
None
See application file for complete search history.

(56) References Cited

U.S. PATENT DOCUMENTS

2012/0189706 A1    7/2012 Copp et al.

FOREIGN PATENT DOCUMENTS

| | | |
|---|---|---|
| CN | 1290429 C | 12/2006 |
| CN | 102764308 A | 11/2012 |
| JP | 04398172 B2 | 1/2010 |
| WO | 2006008115 A1 | 1/2006 |

OTHER PUBLICATIONS

Kusunur Ahamed Basha, et. al., "Effect of dietary supplemented andrographolide on growth, non-specific immune parameters and resistance against Aeromonas hydrophila in Labeo rohita (Hamilton)" Fish & Shellfish Immunology 35 (2013) 1433-1441, Journal Homepage: www.elsevier.com/locate/fsi.
Mohamed El-Boshy, et. al., "Dietary fucoidan enhance the non-specific immune response and disease resistance in African catfish, *Clarias gariepinus*, immunosuppressed by cadmium chloride" Veterinary Immunology and mmunopathology 162 (2014) 168-173, Journal Homepage: www.elsevier.com/loca te/vetimm.
Adrián J. Hernández, et. al., "The effects of supplemented diets with a phytopharmaceutical preparation from herbal and macroalgal origin on disease resistance in rainbow trout against Piscirickettsia salmonis" Aquaculture 454 (2016) 109-117, Journal Homepage: www.elsevier.com/locate/aquaculture.
Qing Yang, et. al., "Effects of dietary fucoidan on the blood constituents, anti-oxidation and innate immunity of juvenile yellow catfish (*Pelteobagrus fulvidraco*)" Fish & Shellfish Immunology 41 (2014) 264-270, Journal Homepage: www.elsevier.com/locate/ fsi.
Pongsak Rattanachaikunsopon, et. al., "Prophylactic effect of Andrographis paniculata extracts against *Streptococcus agalactiae* infection in Nile tilapia (*Oreochromis niloticus*)" Journal of Bioscience and Bioengineering vol. 107 No. 5, 579-582, 2009, www.elsevier.com/locate/jbiosc.
Christopher Marlowe A. Caipang, et. al., "Influence of alginic acid and fucoidan on the immune responses of head kidney leukocytes in cod" Fish Physiol Biochem (2011) 37:603-612.
So Young Kang, et. al., "In vitro Antiviral Activities of Korean Marine Algae Extracts against Fish Pathogenic Infectious Hematopoietic Necrosis Virus and Infectious Pancreatic Necrosis Virus" Food Sci. Biotechnol. vol. 17, No. 5, pp. 1074-1078 (2008).
Ioannis N Vatsos, et. al., "Seaweed extracts as antimicrobial agents in aquaculture" 5th Congress of the International Society for Applied Phycology, J Appl Phycol (2015) 27:2017-2035.

*Primary Examiner* — Susan Hoffman
(74) *Attorney, Agent, or Firm* — JRG Attorneys at Law

(57) ABSTRACT

Veterinary composition comprising an extract of seaweed containing at least 5% fucoidians and an *Andrographis* sp plant extract containing at least 5% of andrographolide, which is useful in the control and prevention of infections produced by intracellular microorganisms in fishes.

9 Claims, 7 Drawing Sheets

Specification includes a Sequence Listing.

VETERINARY COMPOSITION OF MARINE ALGAE AND *ANDROGRAPHIS* SP EXTRACTS, WHICH CAN BE USED TO TREAT INFECTIONS IN FISH

FIELD OF INVENTION

The present invention is referred to a veterinary composition that comprises seaweeds extract with a content of at least 5% of fucoids and an extract of *Andrographis* sp with a content of at least 5% of andrographolide, which is useful in the control and prevention of infections produced by intracellular microorganisms in fishes.

BACKGROUND OF THE INVENTION

It has been known that the aquatic environment in which grows up and cultivates fishes, favors the emergence of diseases. Many measures have been taken for controlling or preventing these diseases, and until now the vaccination, is one of the tools more used for the control of bacterial diseases in fishes. This due to vaccinations show some advantages that begin from their good effectiveness preventing and correcting infections to their low impact in the environment and in the public health, allowing the obtaining of a clean product. In general, this doesn't happen with antibiotics, and among its adverse effects can be mentioned: development of the bacterial resistance; accumulation of antibiotics in the muscle of the fish; contamination of aquatic environments among others.

Nevertheless, the vaccination has disadvantages like it requires of a big manipulation of the fishes, so its practice requires of being careful for not stressing the fishes and doing a little bit effective de vaccination or cause mortality, also adverse effects can be shown like the existence of adherences that can lead to mortalities and decrease in rates of fishes growing. In general, the diseases increase under stress conditions, and certainly, in the intensive production systems used for fish farming, those conditions, are always present. We don't have to forget that aquaculture is the fastest growing sector in the production of food, being one of the main economic activities of this century and with important projections of being the main source of animal protein for human consumption in accordance with the last studies of the FAO.

The losses of production are large and the damages devastating, in the intensive system of production, when the diseases appear.

On the other hand, it is known that efficient vaccination doesn't exist in the prevention of some relevant intracellular pathogens, this is the case of *Piscirickettsia salmonis*, SAV virus, *Francisella noatunensis*, *Renibacterium salmoninarum*, IPNv, in early stages, previous to the vaccination shot. This is due to the intracellular nature of the pathogens, which requires of the activation of an immune answer of the type Th1, activating mainly lymphocytes T cytotoxic, the ones that are in charge of destroying infective cells. The combination of bioactive molecules formed by Fucoidians+ Andropgrapholide, that causes the production by part of the macrophages of cytokines like the IL-12 and IFN, that promote the differentiation of lymphocytes Th0 to Th1, this particularity in their action mechanism, transform the combination in a new tool for prevention and control of intracellular pathogens in salmonids fishes.

The diseases cause in the fishes, symptoms like erosions, warts, eruptions or spots in the skin, flap fraying, inflammation of the abdomen, erratic swimming, bleedings, injuries and ulcers in the pancreas, esophagus, muscle spasms and ascites, among others.

Between the intracellular microorganisms for fishes, we can find: piscirricketssia; viruses such as viral hemorrhage septicemia virus (VHS), infectious pancreatic necrosis virus (IPNv), infectious hematopoietic necrosis virus (IHNV), salmon alphavirus (SAV), infectious salmon anemia (ISAv), and bacteria like *Francicella* sp and *Renibacterium salmoninarum*.

Between diseases cause by these pathogens, that are important in aquaculture we can mention piscirickettsiosis, viral hemorrhage septicemia, infectious pancreatic necrosis, infectious hematopoietic necrosis, sickness of pancreas and sleeping disease, infectious salmon anemia, francisellosis y renibacteriosis.

In particular, since 1989, in the south of Chile, a disease with high mortalities in salmon was detected, called "Sindrome del salmon coho" (salmon coho syndrome), "Sindrome de Huito" (syndrome huito) or piscirickettsiosis (Larenas, J. J.; P. A. Smith; L. H. Garcés; C. Lannan, J. L. Fryer. (1994). Piscirickettsiosis of Atlantic salmon (*Salmo salar*) and coho salmon (*Oncorhynchus kisutch*) inoculated with *P. salmonis*. International Symposium on Aquatic Animal Health. Seattle, Wash.) and which affected various species of salmonids. At the beginning it was found only in the coho salmon, but after affected all the salmonids species cultivated in Chile, causing until a 90% of mortality in some places (Branson E. J., Nieto Díaz-Muñoz D. (1991). Description of a new disease condition occurring in farmed coho salmon, *Oncorhynchus kisutch* (Walbaum), in South America. J Fish Dis; 14: 147-156. Cvitanich J. D., Garate O. N., Smith C. E (1991). The isolation of rickettsia-like organism causing disease and mortality in Chilean salmonids and its confirmation by Koch's postulate. J Fish Dis; 14: 121-145). The disease was found mainly in sea water and estuarine (Fryer J. L, Lannan C. N., Gárces H. L., Larenas J. J., Smith P. A., (1990) Isolation of a rickettsiales-like organism from diseased coho salmon (*Oncorhynchus kisutch*) in Chile. Fish Pathol; 25: 107-114. Branson E. J., Nieto Díaz-Munoz. D. (1991). Description of a new disease condition occurring in farmed coho salmon, *Oncorhynchus kisutch* (Walbaum), in South America. Journal Fish disease: 14: 147-156; Cvitanich J. D., Garate O. N., Smith C. E. (1991). The isolation of rickettsia-like organism causing disease and mortality Chilean salmonids and its confirmation by Koch's postulate. Journal Fish Disease; 14: 121-145) and rarely in sweet water (Gagero A., Castro H., Sandino A. M. (1995). First isolation of *Piscirickettsia salmonis* from coho salmon, *Oncorhynchus kisutch* (Walbaum), and rainbow trout, *Oncorhynchus mykiss* (Walbaum), during the freshwater stage of their life cycle. J Fish Dis; 18: 277-279).

The etiologic agent corresponded to the first isolated rickettsia and characterized from aquatic animals and was called *Piscirickettsia salmonis* (*P. salmonis*). This pathogen is an obligate intracellular parasite, cytopathic for different salmon cell lines and some warm-water fishes. It is Gram negative, pleomorphic, usually coconut, in pairs or in ring shapes and of a size between 0.5-1.5 µm in diameter (Fryer J. L., Lannan C. N., Garcés H. L, Larenas J. J., Smith P. A. (1990) isolation of a rickettsiales-like organism from diseased coho salmon (*Oncorhynchus kisutch*) in Chile. Fish Pathol; 25:107-114).

The clinical signs of the piscirickettsiosis are characterized by swimming on the surface, slowly, erratically and sometimes in a corkscrew way. In addition lethargy, anorexia, shock against the walls of the cage raft, marring and darkening have been described. The most relevant external macroscopic lesions described, include: peeling, branchial pallor, equimotic and petechial bleeding at the base of the fins, nodules an ulcers in the skin up to 2 cm diameter (Bravo, S.; Campos, M. (1989) salmon coho syndrome. Chile Pesquero 54: 47-48; Cubillos V.; Farías, C.; Alberdi, A.; Alvarado, V.; Schafer, W.; Monrás, M. (1990). Anatomopathological characteristics of coho salmon syndrome (S.S.C.), new salmon disease. Animal Patology 4: 14-17; Cvitanich J. D., Garate O. N., Smith C. E. (1991). The isolation of rickettsia-like organism causing disease and mortality in Chilean salmonids and its confirmation by Koch's postulate. Journal Fish Disease; 14:121-145.; Larenas J., Hidalgo L., Garcés H., Fryer J. L., Smith P. (1995). Piscirickettsiosis: injuries in Atlantic salmon (*Salmo salar*) naturally infected with *Piscirickettsia salmonis*. Av Cienc Vet; 10: 53-58). Hematocrit levels reveal severe anemia (Branson E. J., Nieto Díaz-Muñoz D. (1991). Description of new disease condition occurring in farmed coho salmon, *Oncorhynchus kisutch* (Walbaum) in South America Journal Fish Disease; 14: 147-156.).

In the analysis of necropsy of the abdominal cavity, the presence of ascites, renomegaly and splenomegaly was found frequently, subcapsular nodules of creamy to yellowish color in the liver, the presence of a pseudomembrane over the heart and petechial bleeding in the stomach, pyloric blind, intestine, swimming bladder, muscle and visceral fat (Schafer J. W.; Alvarado, V.; Enríquez, R.; Monrás, M. (1990) The coho salmon syndrome (CSS): A new disease in Chilean salmon, reared in sea water. 1990 *Bulletin of the European Association of Fish Pathologists* 10:130.; Larenas J., Hidalgo L., Garćes H., Fryer J. L., Smith P. (1995). Piscirickettsiosis: injuries in Atlantic salmon (*Salmo salar*) naturally infected with *Piscirickettsia salmonis*. Av Cienc Vet; 10: 53-58). In most cases, the intestine was filled with a yellowish mucous content and the stomach with a seromucous transparent liquid (Schafer J. W.; Alvarado, V.; Enriquez R.; Monrás, M. (1990) The coho salmon syndrome (CSS): A new disease in Chilean salmon, reared in see water. 1990 *Bulletin of the European Association of Fish Pathologist* 10:130); The latter gives the impression that the fish has been swallowed some water (Alvarado V.; Schäfer, W.; Enríquez, R.; Monrás, M.; Cubillos, V.; Farías, C.; Alberdi, A. (1990) Salmon Coho Syndrome (S.S.C), new disease of salmonids farmed in seawater phase in Chile. Present Situation. Animal Pathology. 4: 10-13).

From the histopathological point of view, the main injuries were necrosis in different organs and tissues, being the most affected the kidney, liver, spleen and intestine. It was also common to see vascular injuries similar to the mentioned for rickettsias in mammals, like the endothelial necrosis and thrombus formation.

In addition, macrophages containing organisms within the cytoplasm, intravascular coagulation, perivascular inflammation, pericarditis, endocarditis, chronic inflammatory injury in the layer of the intestine, increased granule cell numbers of the intestinal granular stratum and lamellar hyperplasia and fusion were found. (Cubillos V.; Farías, C.; Alberdi, A.; Alvarado, V.; Schäfer, W.; Monrás, M. (1990) Pathological characteristics of the coho salmon syndrome (SSC), new disease of the salmonidae Animal Pathology 4: 14-17, Branson E. J., Nieto Díaz-Muñoz D. (1991) Description of a new disease condition occurring in farmed coho salmon, *Oncorhynchus kisutch* (Walbaum), in South America. Journal Fish Disease; 14: 147-156.; Larenas J., Hidalgo L., Garcés H., Fryer J. L., Smith P. (1995). Pis-cirikckettsiosis: Injuries in Atlantic salmon (*Salmo salar*) naturally infected with *Piscirickettsia salmonis*, Av Cienc Vet, 19: 53-58).

For the diagnosis, smear and tissue staining methods are recommended with Gram, Giemsa, acridine barabha (Cvitanich J. D., Garate O. N., Smith C. E. (1991). The isolation of rickettsia-like organism causing disease and mortality in Chilean salmonids and its confirmation by Koch's postúlate. Journal Fish Disease; 14: 121-145; Lannan C., Fryer, J. (1994) Extracellular survival of *Piscirickettsia salmonis*. *Journal of Fish Diseases* 17:545-548; Office International des Epizooties, OIE. (1997) *Diagnostic manual for aquatic animal diseases*. Paris, Francia, OIE. Pp. 161-168) (1994) and/or toludine blue (Larenas J., Hidalgo L., Garces H., Fryer J. L., Smith P. (1995). Piscirickettsiosis: Injuries in Atlantic salmon (*Salmo salar*) naturally infected with *Piscirickettsia salmonis*, Av Cienc Vet, 10: 53-58). These techniques are suitable for initial routine identification. The indirect immunofluorescence method (IFAT), developed by Lannan et al. (Lannan C. N, Ewing S. A., Fryer J. L (1991)). A fluorescent antibody test for detection of the rickettsia causing disease in chilean salmonids (J Aquat Anim Health, 3: 229-234), is nowadays one of the most sensitive and specific methods for the detection of piscirickettsiosis. This technique has been modified by the use of microwaves (Larenas, J., Astorga, C., Conteras, J., Garces, H., Fryer, J. L, Smith, P. (1996) Rapid detection of *Piscirickettsia salmonis* using microwave irradiation. Fish Pathology 31 (4): 231-232), markedly decreasing the incubation times of the first and second antibody, without varying the specificity and sensitivity.

Another important disease is infectious pancreatic necrosis (IPN), a disease caused by a birnavirus which affects several wild and cultivated aquatic organisms (Reno P W. Infectious pancreatic necrosis and associated aquatic birnaviruses. In: Woo P T K, Bruno D W, editors, Fish Diseases and Disorders. Viral, Bacterial and Fungal Infections. London: CABI Publishing, 1999: 1-55). Salmonidae are mainly affected, so this disease has a significant impact on salmon and trout farming, due to a high mortality of offspring and fry. IPN is on the list of fish diseases of the World Organization for Animal Health (OIE) in its International Aquatic Animal Health Code and should be notified (World Organization for Animal Health (OIE). International health code for Aquatic Animals, France: OIE, 2004).

The causal agent in a virus of the bimavirus family that is icosahedral in shape, approximately 60 nm in diameter (Cerini C P, Malsberger R G, Morphology of infectious pancreatic necrosis virus, Ann NY Acad Sci 1965, 126: 315-319, Dobos P. Size and structure of the genome of infectious pancreatic necrosis virus, Nucleic Acids Res 1976; 3: 1903-1924). It contains a genome composed of two double-stranded ribonucleic acid (RNA) segments. Segment A codifies for two structural proteins (VP2 and VP3) and a non-structural protease, while segment B codifies for an RNA polymerase (Dobos P. Size and structure of the genome of infectious pancreatic necrosis virus Nucleic Acids Res 1976; 3: 1903-1924). The VP2 protein stimulates the production of neutralizing monoclonal antibodies of a specific type (Nicholson B L. Use of monoclonal antibodies in identification and characterization of fish viruses. Annu Rev Fish Dis 1993; 3:241-257) and it is thought that it contains all epitopes recognized by these antibodies (Caswell-Reno P, Reno P W, Nicholson B L. Monoclonal antibodies to infectious pancreatic virus: analysis of viral epitopes and comparison of different isolates. J Gen Virol 1986; 67: 2193-2205). IPNV penetrates through gills and mouth, or through the sensory pores of the lateral line system (Novoa B, J L Barja, A Figueras. 1995. Entry and sequential distribution of an aquatic birnavirus in turbot (*Scophthalmus maximus*). *Aquaculture* 131, 1-9, Chou H Y, TY Peng, S J Chang, Y L Hsu, J L Wu. 1999. Effect of heavy metal stressors and salinity shock on the susceptibility of grouper (*Epinephelus* sp.) to infectious pancreatic necrosis virus. *Vir Res* 63, 121-129). The vertical transmission has been verified in rainbow trout (*Oncorhychus mykiss*) and brown trout (*Salmo trutta*); in other species, cases have been observed associated with infected sexual eggs or fluids, which probably correspond to a vertical infection by external contamination (Reno P W. 1999. Infectious pancreatic necrosis virus and associated aquatic Birnaviruses. In "*Fish Diseases and Disorders*": Viral, bacterial and fungal infections (P T Woo and D W Bruno, eds.), Vol 3, CAB Publishing, Wallingford, U.K., pp 1-55). It has been proposed that vertical infection is also associated with the concentration of viral particles (Rodriguez S, J J Borrego, S I Pérez-Prieto. 2003. Infectious pancreatic necrosis virus: biology, pathogenesis, and diagnostic methods. *Adv Vir Res* 62, 113-165). After a period of undetectable viremia, at four days post-infection approximately necrotic areas are observed in the exocrine pancreas and other organs (Reno P W. 1999. Infectious pancreatic necrosis virus and associated aquatic Birnaviruses. In "*Fish diseases and disorders*": Viral, bacterial and fungal infections (P T Woo and D W Bruno, eds.), Vol 3, CAB Publishing, Wallingford, U.K., pp 1-55); however, the viral distribution may be variable in the different organs Eléout et al., (Eléouet J F, N Druesne, S Chilmonczyk, D Momge, M Dorson, B Delmas. 2001. Comparative study of in-situ cell death induced by the viruses of viral haemorrhagic septicaemia (VHS) and infectious pancreatic necrosis (IPN) in rainbow trout. *J comp Pathol* 124, 300-307) observed that the virus could be found in several organs with the exception of the pancreas, which it may be associated to a different level of tissue tropism that present different isolates viral.

During clinical disease, mortality is inversely proportional to the age of the affected animals (Wolf K. 1988, Infectious pancreatic necrosis. In "*Fish Viruses and Fish Diseases*", Cornell Univ, Press, Ithaca, N.Y., pp 115-157). The most characteristic disease pattern is shown in rainbow trout, brook trout, brown trout, Atlantic salmon and several species of Pacific salmon (Roberts R J, MD Pearson, 2005. Infectious pancreatic necrosis in Atlantic salmon, *Salmo salar* L. *J Fish Dis* 28, 383-389). In offsprings that have normally completed the first feeding, the disease outbreak is usually less explosive, reaching losses of 70% or more over a period of two months. The losses in larger animals can be between 10 and 20% (Roberts R J, M D Pearson. 2005. Infectious pancreatic necrosis in Atlantic salmon, *Salmo salar* L. *J Fish Dis* 28, 383-389).

Generally, affected fishes show anorexia and irregular swimming (swimming on corkscrew way with ataxia lapses). These fishes change to a dark color (hyperpigmentation) and have moderate exophthalmos and abdominal distention. Gills and haemorrhages in the ventral area, the fins included, are also pale. The fishes are thin and have witish "hanging feces" (Wolf K. Fish viruses and fish virus diseases. New York: Cornell University Press, Ithaca, 1988).

According to the main findings of necropsy in offspring, spleen, heart, liver and kidneys are shown pale, and most of the time no food is found in the digestive tract. Petechial haemorrhages are seen in visceras. In some cases, food is found in small amounts, confined to the distal and rectum part of the intestine. Ascitic fluid is frequently seen in the abdominal cavity. In the stomach and intestine can be observed a cohesive milky mucus, among other findings (Wolf K. Fish viruses and fish virus diseases. New York: Cornell University Press, Ithaca, 1988).

The main injuries found in the histopathological study include foci of coagulative necrosis in the pancreas, kidney and intestines. Pancreatic tissue is shown degenerated, even in the acinar areas, with release of the zymogen granules. The nuclei of the acinar cells are observed pyknotics and of variable sizes. In many cases no infiltration of inflammatory cells is shown. (McKnight I J, Roberts R J. The pathology of infectious pancreatic necrosis. I. The sequential histopathology of the naturally occurring condition. Br Vet J 1976; 132:76-85).

In the stomach and intestine, there are variable processes of degeneration and necrosis (Smail D A, N Bain, D W Bruno, J A King, F Thompson, D J Pendrey, S Morrice, C O Cunningham. 2006. Infectious pancreatic necrosis virus in Atlantic salmon, *Salmo salar* L., post-smolts in the Shetland isles, Scotland: virus identification, histopathology, immunohistochemistry and genetic comparison with Scottish mainland isoaltes. *J. fish Dis* 29, 31-41) mucosal detachment (catarrhal enteritis) into the intestinal lumen where epithelial cells with eosinophilic and hyaline cytoplasm and swollen can be observed, many times with their nucleus fragmented, making accumulations of basophilic material, distributed in cellular periphery, showing of a process of apoptosis (McKnight I J, Roberts R J. The pathology of infectious pancreatic necrosis. I. The sequential histopathology of the naturally occurring condition. Br Vet J 1976; 132: 76-85). In the liver, it is possible to find areas of focal or generalized necrosis, which are usually severe in salmon, whereas in rainbow trout are more moderate or insignificant (Roberts R J, M D Pearson. 2005. Infectious pancreatic necrosis in Atlantic salmon, *Salmo salar* L. *J Fish Dis* 28, 383-389).

The virulence, which is the relative ability of the pathogen to cause disease, is a manifestation of the interaction between the adverse effects produced by components of the virus and the defense mechanisms developed by the cells to try to eliminate the infection; however, the result of such interactivity is always determined by the virus through its virulence factors, a function that can be applied by any component of the viral particle (Lyles D, 2000. Cytophatogenesis and inhibition of host gene expression by RNA viruses. *Microbiol and MolBiol Rev* 64, 709-724). The differences in the level of virulence shown between different strains of IPNV have been attributed to their genetic variation (Dobos P. 1995$^a$. The molecular biology of infectious pancreatic necrosis virus. *Annual Rev Fish Dis* 5, 25-54), and with the property of the virus to modify cell signaling pathways through viral proteins encoded by its A segment, able to manipulate cellular machinery to facilitate viral synthesis and avoid the answer of the defense (Hong J R, Y L Hsu, J L Wu. 1999. Infectious pancreatic necrosis virus induces apoptosis due to down-regulation of survival factor MCL-1 protein expression in a fish cell lines. *Virus Res* 63, 75-83; Larsen R, T P Rçkenes, B Robertsen. 2004. Inhibition of infectious pancreatic necrosis virus replication by Atlantic salmon Mx1 protein. *J Virol* 78, 7938-7944). In this sense, the viral proteins considered as the main virulence factors of IPNV are VP2, a component of the outer cover of the viral capsid that participates in the recognition of the virus to the cells; the VP5 protein of inconclusive function, since it has been shown not to be necessary for establishing infection and the viral multiplication, but with anti-apoptotic activity that apparently has no relation in the establishment of the carrier state. Recently, it has been reported that over expression of the VP3 induce apoptosis in cultured cells, but it is difficult to detect in an infection with fully viral particles. However, Vp4 and Vp1 have not been associated with adverse effects at the cellular level, but proteins of similar activity in other viruses have been observed with implication in the pathogenicity of the strains (Lyles D. 2000. Cytopathogenesis and inhibition of host gene expression by RNA viruses. *Microbiol and Mol Biol Rev* 64, 709-724; Liu M, V N Vakharia. 2004. VP1 protein of infectious bursal disease virus modulates the virulence in vivo. Virol 330, 62-73; Nanda S, M Baron. 2006. Rinderpest virus blocks type I and type II interferon action: role of structural and nonstructural proteins. *J Virol* 78, 7555-7568).

During the infection process, the host expresses a varied response aimed at attempting to prevent infection or dissemination of the agent. For this, the non-specific defense system is the most important as a protection measure for fishes, and within this, the interferon system (IFN) is one of the first lines from defense of viral infection through inducing the synthesis of proteins having antiviral activity; in the case of IPNV, the Mx1 protein and the kinase protein dependent of double stranded RNA (PKR) have been shown to have antiviral activity (Roberts R J, MD Pearson. 2005. Infectious pancreatic necrosis in Atlantic salmon, *Salmo salar* L. *J Fish Dis* 28, 383-389). However, it has been reported that some viruses may inhibit or modulate the antiviral response exerted by IFN (Nanda S, M Baron. 2006. Rinderpest virus blocks type I and type II interferon action: role of structural and nonstructural proteins. *J Virol* 80, 7555-7568), which it is supposed also for IPNV (Rodriguez S, J J Borrego, S I Pérez-Ptieto. 2003. Infectious pancreatic necrosis virus: biology, pathogenesis, and diagnostic methods. *Adv Vir Res* 62, 113-165), but it has not been evaluated.

IPNV shows high antigenic and genotypic variability, features that influence the virus-cell interaction, the virulence and the development of the carrier state; however, the mechanisms involved in these processes are not fully determined (Rodriguez S, J J Borrego, SI Pérez-Prieto. 2003. Infectious pancreatic necrosis virus: biology, pathogenesis, and diagnostic methods. *Adv Vir Res* 62, 113-165).

The procedure for the identification of NPI, as recommended by the OIE, is based on the isolation of VNPI in cell culture, followed by the immunological identification of the isolation by immunofluorescence tests (World Organisation for Animal Health. Diagnostic Manual for Aquatic Animal Diseases. France: OIE. 2003), serum neutralisation (Lientz J C, Springer J E. Neutralization test of infectious pancreatic necrosis virus with polyvalent antiserum. J Wildl Dis 1973; 9:120-124) y ELISA (Davis F J, Laidler L A, Perry P W, Rossington D. Alcock R. The detection of infectious pancreatic necrosis virus in asymptomatic carrier fish by an integrated cell-culture and EUSA technique. J Fish Dis 1994; 17:99-110).

The diagnosis of clinical cases is generally based on the histology and immunological evidence of VNPI in the infected tissues. These cases are confirmed by the isolation and immunological identification of the virus by means of such tests (World Organisation for Animal Health. Diagnostic Manual for Aquatic Animal Diseases. France: OIE. 2003). Serological tests in order to identify antibodies against VNPI in infected fishes have not yet been recognized by the OIE (2003), due to insufficient knowledge of the humoral immune response of the fishes to this virus (Wolf K, Quimby M C. Infectious pancreatic necrosis: clinical and immune response of adult trouts to inoculation with five virus J Fish Res Board Can 1969; 26: 2511-2516).

The detection of VNPI in cell lines is consistent and simple, mainly in lines belonging from homologous species. This is because 1) the virus is present in elevated titles in tissues; 2) The isolation can be performed from non-diseased animals; 3) there is no phase in which the virus cannot be isolated; 4) the time required for isolation and identification of the agent is from two to three weeks, which is not critical for the presentation of an epizootic, and 5) high sensitivity and cytopathic effect can be seen easily. The cell lines used for the isolation of VNPI include the RTG-2 (rainbow trout gonad), CHSE-214 (chinook salmon embryo) and BF-2 (bluegill fry) (Kelly R K, Souter B W, Miller H R. Fish cells lines: comparisons of CHSE-214, FHM, and RTG-2 in assaying IHN and IPN viruses. J Fish Res Board Can 1978; 35: 1009-1011)

Nowadays, many methods of detection have been developed by means of the technique of reverse-reaction transcription in the polymerase chain reaction (RT-PCR, by their acronyms in English: reverse transcriptase-polymerase chain reaction) (Rodriguez S-J S, Borrego J J, Perez-Prieto S I. Comparative evaluation of five serological methods and RT-PCR assay for the detection of IPNV in fish. J Viro! Methods 2001; 97:23-31). However, the sensitivity of this technique has not been greater than that of the cell culture, so that isolation of the virus and serological confirmation are the processes of choice for identifying VNPI.

On the other hand, the use of *Andrographis paniculata* is known in the treatment of a wide range of pathologies (Abu-Ghefreh, A. A., Canatan, H. and Ezeamuzie, C. I. (2008) in vitro and in vivo anti-inflammatory effects of andrographolide. International immunopharmacology, 9: 313-318); including diseases such as the common cold, dysentery, fever, tonsillitis, diarrhea, liver diseases, herpes, among others (Patarapanich, C., Laungcholatan, S., Mahaverawat, N., Chaichantipayuth, C., Pummangura, S. (2007) HPLC determination of active diterpene lactones from *Andrographis paniculata* Nees planted in various seasons and regions in Thailand. Thai. J. Pharm. Sci., 31:9). It has anti-inflammatory and antimicrobial properties, (Hai, X., Gui, O., Gai, L., Jun, W. and Hong, L. (2007) Synthesis of andrographolide derivatives: A new family of a-glucosidase inhibitors. Bioorganic & Medicinal Chemistry, 15: 4247-4255), antithrombotic (Zhao, H. Y. and Fang. W. Y. (1991) Antithrombotic effects of *Andrographis paniculata* nees in preventing myocardial infraction. Chin. Med. J., 104 (9): 770-5), hepatoprotective (Siripong, P., Kongkathip, B., Preechanukool, K., Picha, P., Tunsuwan, K. and Taylor, W. (1992) Cytotoxic diterpenoid constituents from *Andrographis paniculata* Nees leaves. J. Sci. Soc. Thailand, 18: 187-194), anti AIDS activity (Chang, R. S., Oing, L., Chen, G. Q., Pan, Q. C. Zhao, Z. L. and Smith, K. M. (1991) Dehydroandrographolide succinic acid monoester as an inhibitor against the human immunodeficiency virus. Proc. Soc. Exp. Bici. Med., 197 (1):59-66), antidiabetic, (Zhang, Z., Jiang, J., Yu, P. Zeng. X., Larrick, J and Wang, Y. (2009) Hipoglycemic and beta cell protective effects of andrographolide analogue for diabetes treatment. J. of T. Medicine, 7:62) and antitumorals (Rao, S., Suseno, G., Matthews, C., Sazali, A., Haji, L., Said, Saad, M., Stevens, M. and Stanslas, J (2007) Semisynthesis and in vitro anticancer activities of andrographolide analogues. Phytochemistry, 68: 904-912).

The plant is extremely bitter in each of its parts (Sheeja, K. and Kuttan. G. (2006) Protectiv effect of *Andrographis paniculata* and andrographolide on cyclophosphamide-induced urothelial toxicity. Integr. Cancer Ther., 5(3): 244-51), however, the aerial portions of *Andrographis paniculata* are used to extract the active principles phytochemicals. The extract contains diterpene, flavonoide, and stigmasters (Koteswara, R., Vimalamma, G., Venkata, R. and Yew, T. (2004) Flavonoids and andrographolides from *Andrographis paniculata*. Phyto., Volume 65, Issue 16, Pages 2317-2321). Being the andrographolide, the first and best isolated active principle, which has been chemically defined as a bicyclic diterpene lactone (thamlikitkul, V., Dechatiwongse, T., Theerapong, S., Chantrakul, C., Boonroj; P., Punkrut, W., Ekpalakorn, W., Bootaeng, N., Yaechaiya, S. and Petcharoen, S. (1991) Efficacy of *Andrographis paniculata*, Nees for pharyngotonsillitis in adults. J. Med. Assoc. Thai., 74 (10): 437-42.

Different of preclinical and clinical studies have been performed to identify the pharmacological properties of the components of *Andrographis paniculata*, for this, both the raw extract of the plant and the purified andrographolide have been used, like the purified Andrographolide. In preclinical studies, the plant extract has shown several activities, such as: hepatoprotective effect administered intraperitoneally in rats (Sharma, A., Lal, K. and Handa, S. (1992) Standarization of the indian crude drug. Kalmegh by high pressure liquid chromatographic determination of andrografolide. Phytochem. Anal., 3, 129-131). antidiarrheal activity in animal models treated with enterotoxin of *Escherichia coli* (Gupta, S., Choudhry, M. A. and Yadava, J. N. S. (1990) Antidiarrhoeal activity of diterpenes of *Andrographis paniculata* (Kal-Megh) against *Escherichia coli* enterotoxin in vivo models Int. J. Crude Drug Res., 28:273-283), and immunostimulatory capacity in mice BALB/c (Puri, A., Saxena, R., Saxena, R. P., Saxena, K. C., Srivastava, V. and Tandon, J. S. (1993) Immunostimulant agents from *Andrographis paniculata*. J. of Natural Products 56:995-999). Another active principle related, but less studied, is the 14-deoxyandrgrapholide which has demonstrated a hypotensive effect (Zhang, C. Y., Kuroyangi, M. and Tan, B. K. H. (1998) Cardiovascular activity os 14-Deoxy-11, 12-didehydroandrographolide in the anesthetized ray and isolated right atria. The Italian Pharmacol. Society, 1:1-5) and anti-inflammatory and antipyretic properties (Zhang, C. Y. and Tan, B. K. H. (1998) Vasorelaxation of rat thoracic aorta caused by 14-deoxyandrographolide. Clin. Exp. Pharmacol. Physiol., 25:424-429).

Other species that may be used instead of *Andrographis paniculata* are: *Andrographis affinis* Nees, *Andrographis beddomei*, *Andrographis echioides* Nees, *Andrographis elongata*, *Andrographis humifusa*, *Andrographis lineata* Nees, *Andrographis macrobotrys* Nees, *Andrographis paniculata* Nees, *Andrographis neesiana*, *Andrographis ovata*, *Andrographis paniculata* Nees, *Andrographis rothii*, *Andrographis serpyllifolia*, *Andrographis viscosula* Nees, *Andrographis viscosula* var, *explicate* y *Andrographis wightiana*.

Also, in a study conducted at the Research Cluster for Health, Southern Cross University of Lismore, Australia, it is reported that extracts of brown algae containing fucoidan, have been shown to have modulating effect of immunity. This study aimed to determine whether marine algae containing a mixture of extracts from three different species of brown algae is safe to administer, and if it has, a biological potential as an immunomodulator. The results allowed to conclude that the complex of nutrients was safe to administer and furthermore that the preparation proved to have potential as an immune modulator effectively (Myers S P, O'Connor J, Fitton J H, Brooks L, Rolfe M, Connellan P, Wohlmuth H, Cheras P A, Morris C. (2001). A combined Phase I and II open-label study on the immunomodulatory effects of seaweed extract nutrient complex. Research Cluster far Health and Wellbeing, Southern Cross University, Lismore, NSW, Australia; 5:45-60).

Numerous studies indicate that sulfated polyanions, mainly heparin, dextran sulfate, lambda and kappa carrageenan xylogalactans, xylomanans and fucoidians, possess potent therapeutic activity against viral diseases like as other anticoagulant and antitumor properties (Chapman V J, Chapman D J. 1980. Seaweed and Their Uses. In: Chapman and Hall (eds). Londres, p 327).

The mechanism of antiviral action of sulfated polysaccharides is primarily inhibiting the entry of enveloped viruses, such as Herpesvirus (HSV), inside of the host cell, by competence for the cell surface receivers (Luscher-Mattli M. 2000. Polyanions a lost chance in the fight against HIV and other virus diseases. Antiviral chemistry; Schaeffer D J, Krylov V S. 2000. Anti-HIV activity of extracts and compounds from algae and cyanobacteria. Ecotoxicology and environmental safety 45:208-227; Witvrouw M, Pannecouque C, De Clercq E. 1997. In: Carbohydrates in drug design, Witczak Z J and Nieforth K A (eds). Marcel Dekker, Inc: New York, pp. 157-207). There is a number of receivers including the heparin sulfate receiver, expressed in various cell types, which provide the incoming points for the Herpes virus. Antiviral activity, in part, is due to the similarity of sulfated polyanions to heparin sulfate molecules in mammals (Campadelli-Fiume et al., 2000).

Fucoidan was tested against several viruses involved in DNA and RNA, such as HSV, HCMV, VSV and HIV, and proved to be a potent and selective inhibitor of these viruses, regardless of their type of nucleic acid (Baba M, Snoeck R, Pauwels R, De Clercq E. 1988. Antimicrob sulfated polysaccharides are potent and selective inhibitors of various enveloped viruses, including herpes simplex virus, cytomegalovirus, vesicular stomatitis virus, and human immunodeficiency virus. Antimicrobial agents and chemotherapy 32:1742-1745; Ponce N M, Pujol C A, Damonte E B, Flores M L, Stortz C A. 2003. Fucoidans from the brown seaweed *Adenocystis utricularis*: extraction methods, antiviral activity and structural studies. Carbohydrate research 338:153-65).

As an example, various immuno-stimulating compositions containing andrographolide or derivatives or fucoidians are disclosed for use in humans, see like an example the following patent literature: WO2005087223, WO9617605, WO2006008115, WO2013117149, CN102399245, RU2381807, CN1939413, CN1939420, JP2005082806, JP2002265370, WO0185709, WO0185710, US2002032229, JPH11228602, JPH01313433. Also, immuno-stimulating pharmaceutical compositions of fucoidans and chitosan, and fucoidians and lactobacillus, are known see like an example JP2005060327 and JP2010235528.

Also, vaccines for fish comprising fucoidians are known, see JP2006312595.

The prior art also discloses various immunostimulatories, nutritional compositions or others to treat and prevent diseases in humans, which comprise terpenes or their derivatives and flavonoids and their derivatives, see like a way of example, the following patent literature: WO2005020881, U.S. Pat. Nos. 5,108,750, 4,906,471, 4,842,859, WO2014201637, CN103923795, CN103735654, CN103417630, CN103005447, MX2011002765, CN102614228 and EA201001289.

The prior art also discloses compositions comprising terpenes or their derivatives and flavonoids and their derivatives in order to restore the color of cultured fishes or to pigment them, promote their growth or the foods that enhance their immunity, see like a way of example the following patent literature: JPH4166040, WO2006123939, JP2010124768 and CN103355491.

Likewise, antiviral or sporozoal compositions are known, comprising terpenes or their derivatives and flavonoids and their derivatives, are known to treat fishes diseases, see like a way of example the following patent literature: CN103989865 and KR20120118805.

However, the present invention relates to a synergistic immunostimulating composition for fishes comprising fucoidians and andrographolide.

Regarding the fucoidians it is important to point out that they belong from different species of brown algae, and they differ in accordance to the orders corresponding to brown algae.

Thus, the fucal order comprises the binding of Fucose units which varies according to the species to be analyzed but mainly shows glycosidic bonds of the type (1→3) or (1→4) and the sulfated groups can be located in the positions C-2, C-3 or C-4. Examples of algae from which fucoids can be obtained from the fucal order are: *Fucus vesiculosus, Fucus evanescens, Fucus distichus, Fucus serratus, Pelvetia Ascophylium nodosum, Himanthalia Lorea, Bifurcaria bifurcata, Sargassum stenophylfum, Hizikia fusiforme* y *Durvillaea antárctica.*

In the order Laminare and another brown algae, the binding of Fucose units varies by species but mainly shows glycosidic bonds of the type (1→2) or (1→3) and the sulfated groups can be located in the positions C-2 or C-4. It is also mentioned that the Galactan fraction present is given by bonds (1→3) and (1→6) with sulphated groups especially in the position C-4. Examples of algae from which fucoids of laminar order and other brown algae can be obtained are: *Lessonia nigrescens, Lessonia trabeculata, Lessonia vadosa, Macrocystis pyrifera, Undaria pinnatifida, Padina pavonia, Laminaría angustata, Laminaría japónica, Ecklonia kurome, Adenocytis utricularis, Dictyota menstrualis, Spatoglossum schroederi* y *Chordaria flagellifonnis.*

BRIEF DESCRIPTION OF THE INVENTION

The present invention relates to a synergistic immunostimulating composition for fishes comprising fucoidians and andrographolide. More preferably, the present invention relates to a synergistic immunostimulating composition for fishes comprising fucoidians and andrographolide, and allowing effective control and prevention of infections produced by intracellular microorganisms. Still more particularly, the present invention relates more closely to a synergistic composition comprising fucoidians and andrographolide, and allowing effective control and prevention of piscirickettsiosis and infectious pancreatic necrosis (IPN) in fishes.

DETAILED DESCRIPTION OF THE INVENTION

Figure 1:
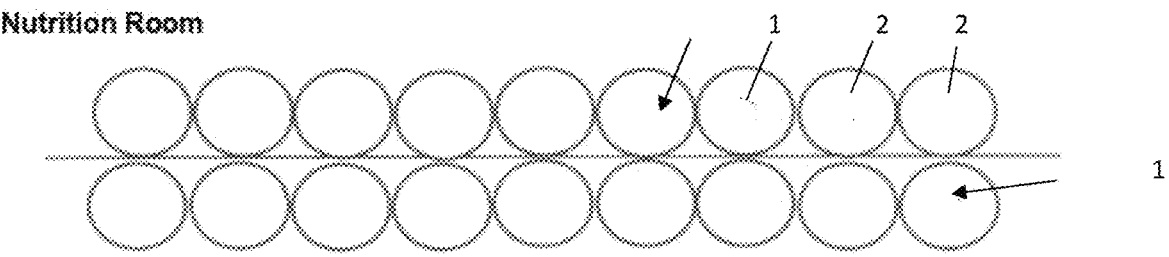
FIG. 1. It illustrates the conformation of distribution in fish ponds prior to challenge with *P. salmonis*, where (1) DE indicates the diet with the composition of the present invention and (2) C means the diet without the composition of the present invention.

The present invention is related with a synergistic immunostimulant composition for fishes that comprise fucoidians and andrographolide, where the fucoidians are obtained from extracts prepared from *Fucus vesiculosus, Fucus evanescens, Fucus distichus, Fucus serratus, Pelvetia wrightii, Ascophyllum nodosum, Himanthalia Lorea, Bifurcaría bifurcata, Sargassum stenophylum, Hizikia fusiforme, Durvillaea antártica, Lessonia nigrescens, Lessonia trabecu-*

*lata, Lessonia vadosa, Macrocystis pyrifera, Undaria pinnatifida, Padina pavonia, Laminaria angustata, Laminaria japónica, Ecklonia kurome, Adenocytis utricularis, Dictyota menstrualis, Spatoglossum schroederio Chordaria flagelliformis.* While the andrographolide are obtained from extracts prepared belonging from *Androgaphis affinis* Nees, *Andrographis beddomei, Andrographis echioides* Nees, *Andrographis elongata, Andrographis humifusa, Andrographis lineata* Nees, *Andrographis macrobotrys* Nees, *Andrographis nallamalayana, Andrographis neesiana, Andrographis ovata, Andrographis paniculata* Nees, *Andrographis, rothii, Andrographis serpyllifolia, Andrographis viscosula* Nees *Andrographis viscosula* var. *explicata* y *Andrographis wightiana*. In the synergistic immunostimulating composition, the ratio fucoidian to andrographolide is in the range of 5:95 to 20:80. Preferably, the ratio fucoidian to andrographolide is 10:90.

The present invention is related mainly to a synergistic immunostimulating composition for fishes comprising fucoidians and andrographolide, which allows an effective control and prevention of infections produced by intracellular microorganisms.

The present invention is related more particularly to a synergistic composition comprising fucoidians and andrographolide, which allows an effective control and prevention of piscirickettsiosis, viral haemorrhagic septicemia, infectious pancreatic necrosis, infectious haematopoietic necrosis, pancreas disease and sleeping disease, infectious anemia of salmon, francicellosis and renibacteriosis.

The present composition comprises synergistic comprising fucoidian and andrographolide, which allow effective control and prevention of piscirickettsiosis and infectious pancreatic necrosis (IPN) in fishes.

Example 1

Preparation of Aqueous Flour Extract Containing Fucoidian

The dried brown algae were first pulverized by freezing them in liquid $N_2$, and using a porcelain mortar, to obtain a 300 micron algae powder.

Ten grams of the ground dried algae mixture were extracted with 200 ml of distilled water with continuous stirring for 4 hours at 25° C. The algal tissue was removed by simple filtration. The aqueous extract was centrifuged until a clarified solution. The solution is precipitated by the addition of 3 volumes of ethanol. The precipitate was recovered by centrifugation and dried in an electric oven at 50° C.

Example 2

Preparation of Andrographolide and Preparation of Extract

For the preparation of the extract of andrographolide, dried leaves of *Andrographis* sp were used, the extraction was carried out using an 80% v/v water-ethanol mixture, the final extract is a composition containing 80% of the native extract and 20% of maltodextrin.

Example 3

Preparation of a Composition Andrographolide and Fucoidan

A mechanical mixture of both dry extracts was performed in a ratio of 90/10 of algae extract (fucoidan) and extract of *Andrographis* sp., respectively. For this, a KitchenAid Heavy Duty mixer (Model KS5SS, USA) was used with stainless steel container, adjustable speed and capacity >1.5 L. The selected mixing speed was, according to the equipment, level 2 equivalent to ±70 rpm of the upper shaft. The mixing time was 10 minutes, the mixture was prepared according to the proportions of ingredients and the densities of these were determined through a gravimetric method with results of 0.77 grs/cm$^3$.

Example 4

Results of Immune Effect in Fucoidan Cell Lines

The SHK-1 cell line, derived from *Salmo salar's* kidney, was used. The assay was started when the cells shown 90% of confluence, and then they were stimulated with algae extract (5% of Fucoidian).

The treatment was applied independently to SHK-1 cells, in L15 medium supplemented with 10% fetal bovine serum at a dose of 1 µg/ml, the cells were incubated at 20° C. during 24 hours of stimulation time.

After the treatment, the cell supernatant was discarded and the cells were lysed with 200 µl of TRK lysis buffer and stored in tubes of 1.5 ml at −80° C. RNA extraction from the cells was performed using the RNA extraction kit (Omega-bio-tek), according to the manufacturer's protocol.

Once the total RNA was obtained, the mRNAs were transformed into cDNA by means of the reverse transcription reaction, which was performed in a total volume of 20 µl of solution, divided in two parts. The first reaction was performed in a mixture containing 1.6 µl of oligo-dT (1.25 µg/ml) for analysis of gene expression of the markers 1.0 µl of dNTPs (10 mM); 8.0 µl of total RNA (5 µg) and 0.1 µl of nuclease-free water and it was incubated for 10 min at 60° C. to elute secondary structures of the mRNAs. Subsequently, a second mixture comprised of 1 µl of M-MLV reverse transcriptase (200 U), 4 µl of 5× enzyme buffer and 0.5 µl of recombinant RNAseOUT ribonuclease inhibitor (40 U) was added to the solution, in a total volume of 5.5 µl and it will be incubated for 1 h at 37° C. Finally for the inactivation of reverse transcriptase, the reaction mixture was incubated at 72° C. during 10 min. The synthesized cDNA was stored at ~20° C. for its subsequent amplification for PCR or its quantification by real-time (qPCR) for IFN-1 and IL-12 genes relative to EF-1α expression using the primers listed in Table 1 below:

TABLE 1

| Gen | Primers | Genbank |
|---|---|---|
| IFN-I | Fwd TGGGAGGAGATATCACAAAGC (SEQ ID No: 1)<br>Rev TCCCAGGTGACAGATTTCAT (SEQ ID No: 2) | AY216594 |
| IL-12 | Fwd CTGAATGAGGTGGACTGGTATG (SEQ ID No: 3)<br>Rev ATCGTCCTGTTCCTCCG (SEQ ID No: 4) | BT049114 |
| ELF-1 | Fwd TGCCCCTCCAGGATGTCTAC (SEQ ID No: 5)<br>Rev CACGGCCCACAGGTACTG (SEQ ID No: 6) | AF321836 |

Each amplification reaction was performed using 2 µl of cDNA as the annealing, 0.2 µM (Table 1) primers, 0.8 µl MgCl$_2$ (25 mM), 1 µl Lightcycler® Fast Start DNA Master SYBR Green amplification mixture in a volume of 10 µl. The reaction was carried out in a LightCycler® 1.5 thermal cycler. The program consists of the following steps: initial denaturation at 95° C. for 10 min, followed by a PCR reaction of 35 cycles each composed of denaturation at 95° C. for 10 seconds, mating at 58° C. for 10 seconds and extension at 70° C. for 10 seconds. Subsequently a cycle to obtain the melting curve for 20 s at 95° C., and finally a cooling cycle at 40° C. for 30 s. For the relative quantification, it was performed with a standard curve, consisting of reactions containing dilutions of the purified PCR product of known concentration for the gene of interest. After obtaining and quantifying the PCR product corresponding to each gene, dilutions were made in a range of $10^7$ to $10^2$ numbers of copies/µl for each gene under study, for the subsequent calculation of the efficiency of the reaction, where the following relation, E=10(−1/slope)−1 will be used. For the calculation of relative expression by the qPCR technique amplification reactions of the ELF-1 gene cDNA were performed on each RNA sample from cells treated with the different stimuli in vitro. Then, the expression changes were calculated using the comparative CT method (Pfaffl, 2001).

Figure 3:
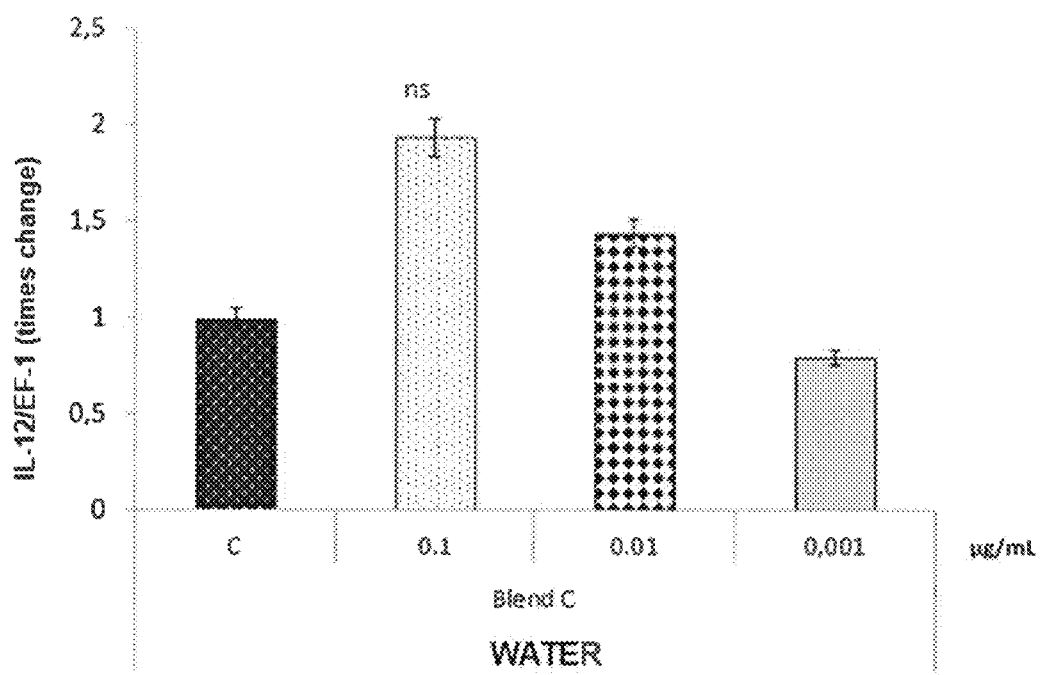
FIG. 3. It illustrates the expression analysis of IL-12 in SHK-1 cells treated with algae extract (FUTERPENOL®, A composition of botanic extracts and derivated of seaweeds with bioactive molecules that promote immunity against intracellular pathogens), at different concentrations (0.01-1 μg/ml) and re-suspended in ethanol and water. Analysis of the effect of IL-12 expression was performed at 4 hours post-treatment in SHK-1 cells treated with the extract 0.001 μg/mL, 0.01 μg/mL and 0.1 μg/mL. The results show the averages±standard error of triplicate samples. The • indicate significant differences in relation to the control without stimulus, analyzed by t-student, p<0.05, ns, not significant.

The results are illustrated in FIG. 3.

Example 5

Result of Immune Effect in Andropgrapholide Cell Lines

The SHK-1 cell line, derived from Salmo's kidney, was used. The assay was started when the cells showed 90% confluency, where they were stimulated with an extract of *Andrographis* sp (10% total Andrographolide).

The treatment was applied independently to SHK-1 cells in L15 medium supplemented with 10% fetal bovine serum at a dose of 5 nM of the *Andrographis* sp extract, the cells were incubated at 20° C. for 24 hours of stimulation time.

After the treatment was finished, the cell supernatant was discarded and the cells were lysed with 200 µl of TRK lysis buffer and stored in 1.5 ml tubes at −80° C. RNA extraction from the cells was performed using the RNA extraction kit (Omega-bio-tek), in accordance to the manufacturer's protocol.

Once the total RNA was obtained, the mRNAs were transformed into cDNA by means of the reverse transcription reaction, which was performed in a total volume of 20 µl of solution, divided into two parts. The first reaction was performed in a mixture containing 1.6 µl of oligo-dT (1.25 µg/ml) for analysis of gene expression of the 1.0 µl markers of dNTPs (10 mM); 8.0 µl of total RNA (5 µg) and 0.1 µl of water free of nucleases and incubated for 10 min at 60° C. to remove secondary structures from the mRNAs. After this a second mixture comprised of 1 µl of M-MLV reverse transcriptase (200 U), 4 µl of 5× enzyme buffer and 0.5 µl of RNAsaOUT 40 U recombinant ribonuclease inhibitor was added to this solution, in a total volume of 5.5 µl and it will be incubated for 1 h at 37° C. Finally for inactivation of reverse transcriptase, the reaction mixture was incubated at 72° C. for 10 min. The synthesized cDNA was stored at −20° C. for subsequent PCR amplification or quantification by real-time PCR (qPCR) for the IFN-1 and IL-12 genes relative to the expression of EF-1α using the primers indicated in Table 2 below:

TABLE 2

| Gen | Primers | Genbank |
|---|---|---|
| IFN-I | Fwd TGGGAGGAGATATCACAAAGC (SEQ ID No: 1) Rev TCCCAGGTGACAGATTTCAT (SEQ ID No: 2) | AY216594 |
| IL-12 | Fwd CTGAATGAGGTGGACTGGTATG (SEQ ID No: 3) Rev ATCGTCCTGTTCCTCCG (SEQ ID No: 4) | BT049114 |
| ELF-1 | Fwd TGCCCCTCCAGGATGTCTAC (SEQ ID No: 5) Rev CACGGCCCACAGGTACTG (SEQ ID No: 6) | AF321836 |

Each amplification reaction was performed using 2 µl CDNA as a template, primers of 0.2 µM (Table 2), 0.8 µl MgCl 2 (25 mM), 1 µl Lightcycler® Fast Start DNA Master SYBR Green amplification mixture in a volume of 10 µl. The reaction was carried out in a LightCycler® 1.5 thermal cycler. The program consisted on the following steps: initial denaturation at 95° C. during 10 min, followed by a PCR reaction of 35 cycles each one composed of denaturation at 95° C. during 10 s, mating at 58° C. during 10 s and an extension at 70° C. during 10 s. Subsequently a cycle to obtain the melting curve for 20 s at 95° C. And finally a cooling cycle at 40° C. during 30 s. The relative quantification was performed with a standard curve, consisting of reactions containing dilutions of the purified PCR product of a concentration known for the gene of interest. After obtaining and quantifying the PCR product corresponding to each gene, successive dilutions were performed in a range of $10^7$ to $10^2$ numbers of copies/µl for each gene under study, for the subsequent calculation of the efficiency of the reaction, where the following relation, E=10(−1/slope)−1 will be used. For the calculation of relative expression by the qPCR technique amplification reactions of the ELF-1 gene cDNA were performed on each RNA sample from cells treated with the different stimuli in vitro. Then, the expression changes were calculated using the comparative CT method (Pfaffl, 2001).

Figure 4A:
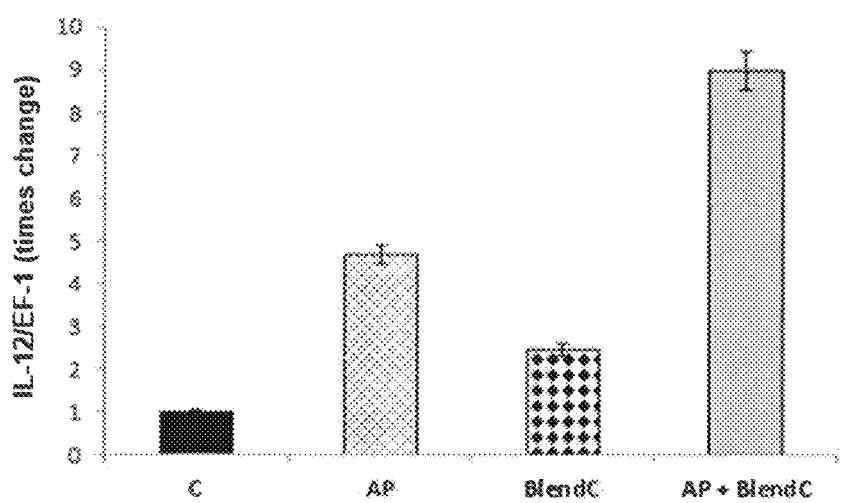
FIGS. 4A and 4B. Illustrates the analysis of the expression kinetics of IL-12 (4A) and IFN-1 (4B) in SHN-1 cells treated with 0.5 nM Andrographolide (AP), 1 μg/ml seaweed extract (BC), the composition of the invention (AP+BC) and diet alone as control (C). Analysis of the effect of IL-12 and IFN-1 expression was performed on SHK-1 cells treated with the composition of the present invention. The differences were statistically significant in relation to the t-Student control. •p<0.05, n=3.
Figure 4B:
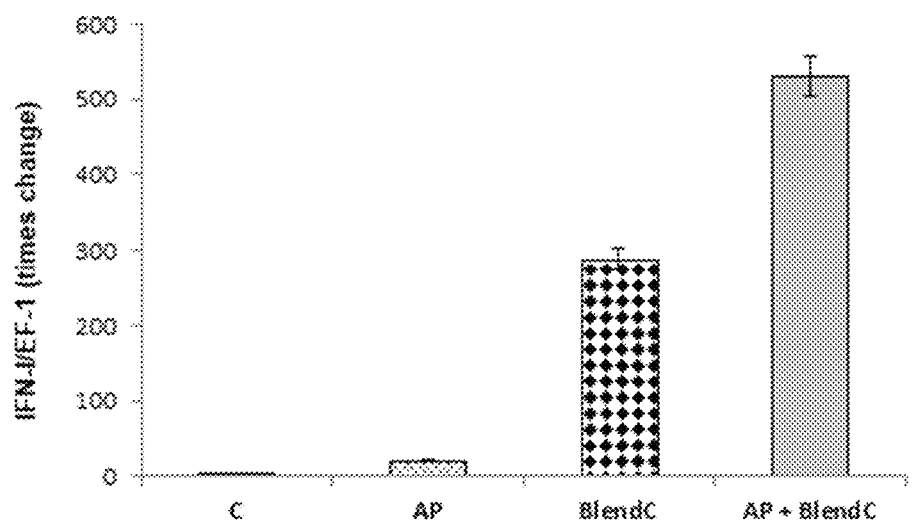

The results are illustrated in FIGS. 4A and 4B.

Example 6

Result of Immune Effect on Cell Lines of the Mixture Fucoidian Plus Andrographolide The SHK-1 cell line, derived from *Salmo salar's* kidney, was used. The assay was started when the cells had 90% confluence, where they were stimulated with an extract of *Andrographis* sp and an extract of brown algae.

The treatment was applied at the same time to SHK-1 cells, in a half of L15 supplemented with 10% fetal bovine serum at doses of 1 µg/ml of brown algae extract (5% total fucoidians) and 5 nM extract of *Andrographis* sp (10% total andrographolide) cells were incubated at 20° C. during 24 hours of stimulation time.

After treatment, the cell supernatant was discarded and cells were lysed with 200 µl of TRK lysis buffer and stored in 1.5 ml tubes at −80° C. RNA extraction from the cells was performed using the RNA extraction kit (Omega-bio-tek), according to the manufacturer's protocol.

Once the total RNA was obtained, the mRNAs were transformed into cDNA by means of the reverse transcription reaction, which was performed in a total volume of 20

μl of solution, divided in two parts. The first reaction was performed in a mixture containing 1.6 μl of oligo-dT (1.25 μg/ml) for analysis of gene expression of the 1.0 μl markers of dNTPs (10 mM); 8.0 μl of total RNA (5 μg) and 0.1 μl of water free of nucleases and it was incubated during 10 min at 60° C. to remove secondary structures from the mRNAs. Subsequently, to this solution was added a second mixture comprised of 1 μl of M-MLV reverse transcriptase (200 U), 4 μl of 5× enzyme buffer and 0.5 μl of recombinant RNAse-OUT ribonuclease inhibitor (40 U), in a total volume of 5.5 μl and it will be incubated during 1 h at 37° C. Finally for inactivation of reverse transcriptase, the reaction mixture was incubated at 72° C. during 10 min. The synthesized cDNA was stored at −20° C. for further amplification by PCR or quantification by real-time PCR (qPCR) for the IFN-1 and IL-12 genes relative to EF-1α expression using the primers indicated in Table 3 below:

TABLE 3

| Gen | Primers | Genbank |
|---|---|---|
| IFN-I | Fwd TGGGAGGAGATATCACAAAGC (SEQ ID No: 1) Rev TCCCAGGTGACAGATTTCAT (SEQ ID No: 2) | AY216594 |
| IL-12 | Fwd CTGAATGAGGTGGACTGGTATG (SEQ ID No: 3) Rev ATCGTCCTGTTCCTCCG (SEQ ID No: 4) | BT049114 |
| ELF-1 | Fwd TGCCCCTCCAGGATGTCTAC (SEQ ID No: 5) Rev CACGGCCCACAGGTACTG (SEQ ID No: 6) | AF321836 |

Each amplification reaction was performed using 2 μl of cDNA as a template, primers of 0.2 μM (Table 3), 0.8 μl MgCl (25 mM), 1 μl Lightcycler® Fast Start DNA Master SYBR Green amplification mixture in a volume of 10 μl. The reaction was carried out in a LightCycler® 1.5 thermal cycler. The program consisted of the following steps: initial denaturation at 95° C. during 10 min, followed by a PCR reaction of 35 cycles each composed of denaturation at 95° C. during 10 s, mating at 58° C. during 10 sec and extension at 70° C. during 10 sec. Subsequently a cycle to obtain the melting curve during 20 s at 95° C., and finally a cooling cycle at 40° C. during 30 s. The relative quantification was performed with a standard curve, consisting of reactions containing dilutions of the purified PCR product of known concentration for the gene of interest. After obtaining and quantifying the PCR product corresponding to each gene, successive dilutions were performed in a range of $10^7$ to $10^2$ number of copies/μl for each gene under study, for the subsequent calculation of the efficiency of the reaction, where the following relation, E=10(−1/slope)−1 will be used. For the calculation of the relative expression by the qPCR technique amplification reactions of the ELF-1 gene cDNA were performed in each RNA sample from cells treated with the different stimuli in vitro. Then, the expression changes were calculated using the comparative CT method (Pfaffl, 2001).

The results are illustrated in FIGS. 4A and 4B.

Example 7

Result of Immune Effect by Challenge P. salmonis

The SHK-1 cell line, derived from *Salmo salar*'s kidney, was used. The assay was started when the cells showed a 90% of confluence, where they were stimulated with a combination that will ensure a concentration of the brown algae extract of 1 μg/ml and 5 nM of the extract of *Andrographis* sp, as well as the individual stimulation with a concentration of 1 μg/ml extract of brown algae, and individual stimulation with a concentration of 5 nM of the extract of *Andrographis* sp. The treatments were applied independently to SHK-1 cells in L15 supplemented with 10% fetal bovine serum at the above-mentioned doses, cells were incubated at 20° C. during 24 hrs incubation.

Infection with *P. salmonis* was carried out after the incubation period. For the challenge, a strain of *Piscirickettsia salmonis* PPT005 grown on a SHK-1 cell line, which was originally isolated from a dying population of Atlantic salmon (*Salmo salar*) from a farm salmond center near Puerto Montt, Chile, using CHSE-214 cells. The cells were infected and incubated at 18° C. in L-15 medium supplemented with 2% SFB. The bacteria were harvested from the infected cells when they had a 90% cytopathic effect (CPE). Finally, functional assays were performed by sowing $10^4$ bacteria per mL in SHK-1 cells at 90% of confluence.

The length of the challenge test was 9 days, time required to obtain a 50% cytopathic effect in the control monolayers. After the treatment was complete, the supernatants were harvested and the surviving cells were lysed with 200 μl of TRK lysis buffer and stored in tubes of 1.5 ml at −80° C.

Figure 5:
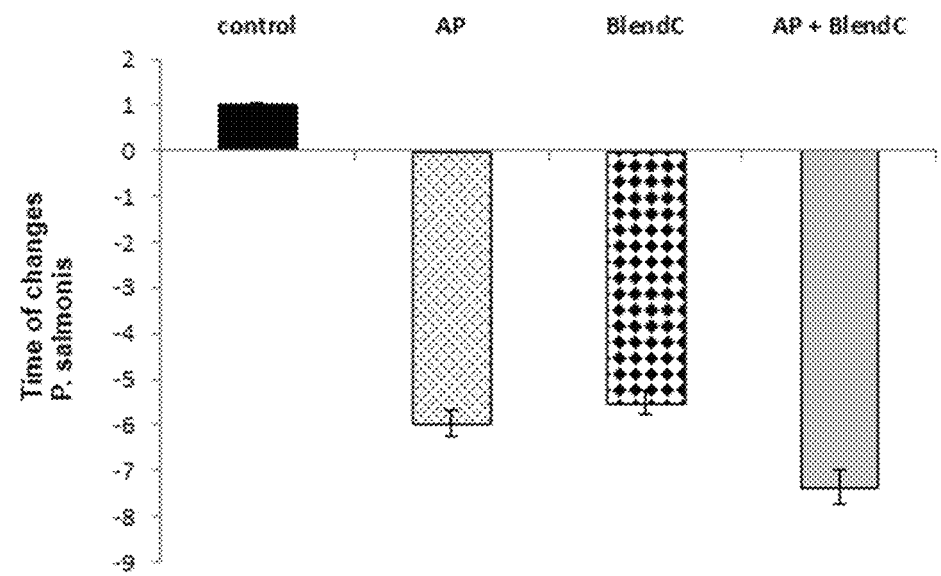
FIG. 5. It illustrates the detection of *P. salmonis* in cells surviving the infection. The bacterial change was determined in SHK-1 cells treated with 0.5 nM Andrographolide (AP), 1 μg/ml seaweed extract (BlendC), the composition of the invention (AP+BlendC) and the diet alone as control (C). This analysis was determined based on the differences of Ct. The differences were statistically significant in relation to untreated cell control and infected with *P. salmonis*, t-Student. *p<0.05, n=3.

1 ml of each culture supernatant from SHK-1 cells was taken with 9 days of infection. These supernatants were centrifuged at 700×g during 10 min to remove the cell residue, and then at 16,000×g for 45 min to recover the bacteria in an Eppendorf 5402 centrifuge. All the sediments were processed by the Chelex method for obtaining the DNA to amplify. Briefly, they were suspended in 100 μl of 6% Instagene p/v (Chelex 100, Bio-Rad), they were shaken at maximum speed in a vortex and centrifuged at 11,600×g during 5 min in an Eppendorf centrifuge to collect the pearls of Chelex in the sediment and DNA in the supernatant. For the estimation of bacterial numbers, standard numbers were used like reference with known numbers of *P. salmonis* copies, obtained by cloning the ITS of this bacterium in the vector pCR® 2.1 TOPO TA (Invitrogen). The standards of $10^4$ to $10^{10}$ number of copies and the DNAs obtained by Chelex were amplified in parallel. Each reaction was performed in a volume of 30 μl with 1 μg of each DNA sample, and 0.5 mM of the ITS primers (Marshall et al 1998) labeled with FAM (495-535 nm). For amplification an initial denaturation of 10 minutes at 95° C. was performed, followed by 35 cycles with the following segments: denaturation at 95° C. during 15 seconds, alignment at 60° C. during 30 seconds and an extension at 72° C. during 45 seconds, and then a final extension of 6 min at 72° C. From the amplification curves obtained for each sample, the Ct (crossing threshold) values of the copy number standards were estimated, in accordance to the method described by Phaffi, 2001, the results are plotted in FIG. 5. In the case of the suriing cells a RNA extraction from the cells was performed using the RNA extraction kit (Omega-bio-tek), in accordance to the manufacturer's protocol.

Once the total RNA was obtained, the mRNAs were transformed to cDNA by means of the reverse transcription reaction, which was performed in a total volume of 20 μl of solution, divided into two parts. The first reaction was carried out in a mixture containing 1.6 μl of oligo-<1T (1.25 μg/ml) for analysis of gene expression of the markers 1.0 μl of dNTPs (10 mM); 8.0 μl of total RNA (5 μg) and 0.1 μl of water free of nucleases and it was incubated during 10 min at 60° C. to remove secondary structures from the mRNAs.

After, a second mixture comprised of 1 µl of M-MLV reverse transcriptase (200 U), 4 µl of 5× enzyme buffer and 0.5 µl of recombinant RNAseOUT ribonuclease inhibitor (40 U) was then added to this solution, in a total volume of 5.5 µl and it will be incubated during 1 h at 37° C. Finally for inactivation of the reverse transcriptase, the reaction mixture was incubated at 72° C. during 10 min. The synthesized cDNA was stored at −20° C. for subsequent PCR amplification or quantification by real-time PCR (qPCR) for the IFN-1 and IL-12 genes related to EF-1α expression using the primers indicated in table 4 below:

TABLE 4

| Gen | Primers | Genbank |
|---|---|---|
| IFN-I | Fwd TGGGAGGAGATATCACAAAGC (SEQ ID No: 1) Rev TCCCAGGTGACAGATTTCAT (SEQ ID No: 2) | AY216594 |
| IL-12 | Fwd CTGAATGAGGTGGACTGGTATG (SEQ ID No: 3) Rev ATCGTCCTGTTCCTCCG (SEQ ID No: 4) | BT049114 |
| ELF-1 | Fwd TGCCCCTCCAGGATGTCTAC (SEQ ID No: 5) Rev CACGGCCCACAGGTACTG (SEQ ID No: 6) | AF321836 |

Each amplification reaction was performed using as a template 2 µl of cDNA, 0.2 µM primers (Table 1), 0.8 µl MgCl2 (25 mM), 1 µl of Lightcycler® Fast Start DNA Master SYBR Green amplification mixture in a volume of 10 µl. The reaction was carried out in a LightCycler® 1.5 thermal cycler. The program consisted of the following steps: initial denaturation at 95° C. during 10 min, followed by a PCR reaction of 35 cycles each one composed of denaturation at 95° C. during 10 s, mating at 58° C. during 10 s and extension at 70° C. during 10 s. Subsequently a cycle to obtain the melting curve during 20 s at 95° C., and finally a cooling cycle at 40° C. during 30 s. Relative quantification was performed with a curve standard, consisting of reactions containing dilutions of the purified PCR product of known concentration for the gene of interest. After obtaining and quantifying the PCR product corresponding to each gene, successive dilutions were performed in a range of $10^7$ to $10^2$ number of copies/µl for each gene under study, for the subsequent calculation of the efficiency of the reaction, where the following relationship, E=10 (−1/slope)−1. For the calculation of the relative expression by the qPCR technique amplification reactions of the ELF-1 gene cDNA were performed on each RNA sample of cells treated with the different stimuli in vitro. Then, the expression changes were calculated using the comparative CT method (Pfaffl, 2001).

Example 8

Immunostimulation Against Intracellular Microorganisms (IPNv) with the Composition of the Present Invention in Salmonid Fishes Cell Lines A study was performed on salmonid fishes cell lines, where the composition of the present invention was evaluated. Cell lines exposed to the combination of fucoidians+ Andrographolide, cell lines exposed only to fucoidians, and subsequently, molecular markers relevant in Th0 to Th1 differentiation such as IL-12 and IFN-1 were evaluated. The separate fucoidians and the combination of these ones+ Andrographolide are significantly different in surviving cells following a challenge with IPNV. At the same time, there is a decrease in the copy numbers of the pathogen agents significantly higher than the cells that received the composition of the present invention in relation to the use of only the fucoidians or the aqueous extract of brown algae.

Figure 6A:
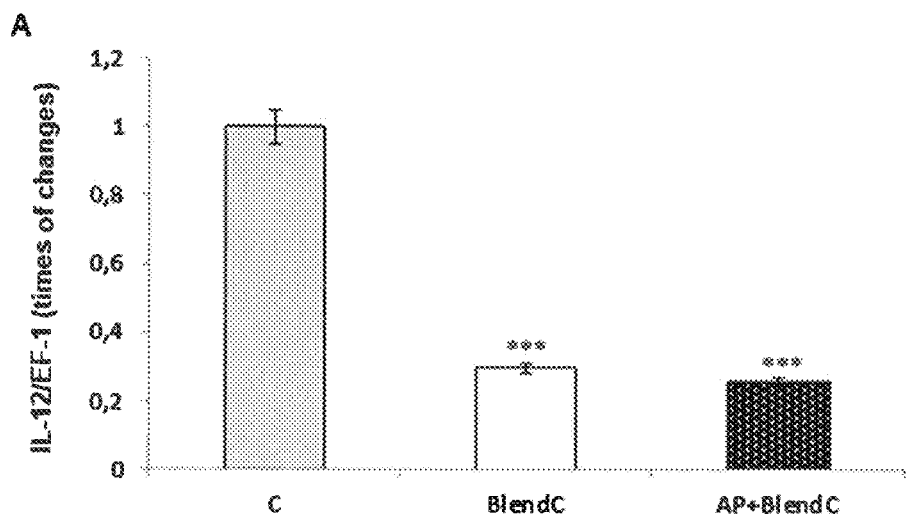
FIGS. 6A and 6B. It illustrates the analysis of the expression of IL-12 (6A) and IFN-I (6B) on surviving cells to the infection with IPNv: The expression of IL-12 and IFN-I was done in SHK-1 cell treated with seaweed (BlendC) 1 μg/ml, the composition of the invention (AP+BlendC) and the diet alone as a control (C) and infected by the virus. The differences were statistically significant in relation to control *p<0.05, n=3.
Figure 6B:
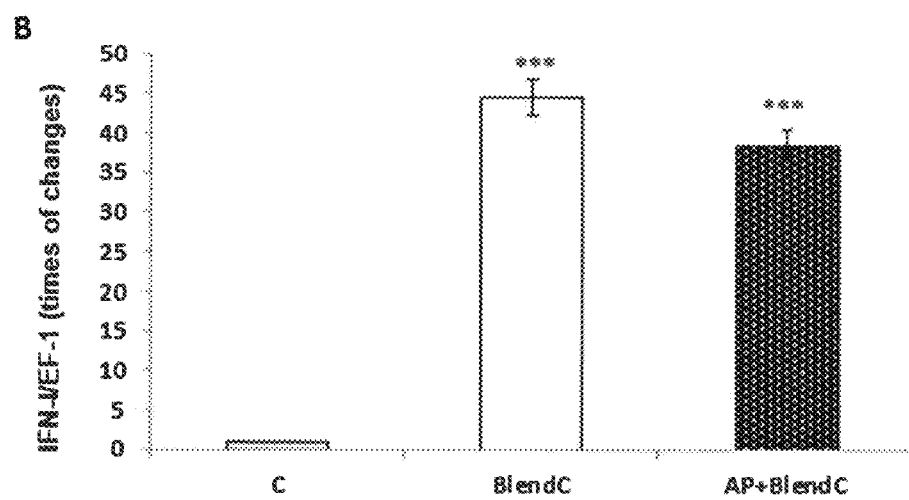
Figure 7:
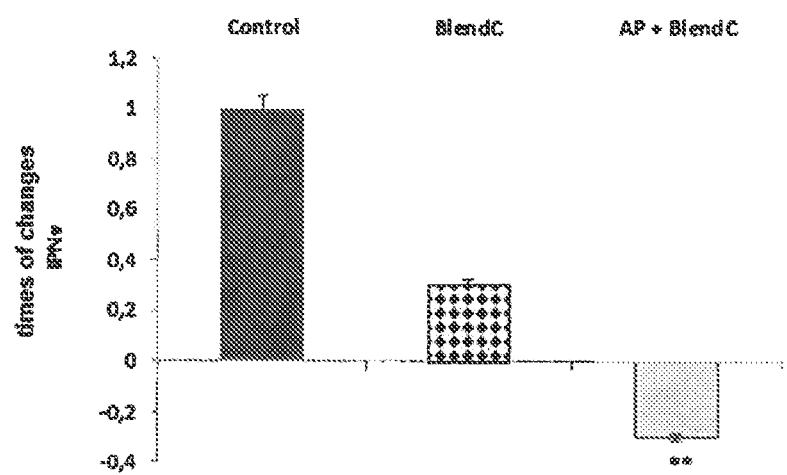
FIG. 7. It illustrates the detection of IPNv in surviving cell from the infection. The virus-shifting times were determined on SHK-1 cells treated with the seaweed extract (BlendC) 1 μg/ml, and the diet alones as a control (C). This analysis was determined on the basis of the differences of Ct. The differences were statistically significant in relation to the control of cells without treatment or infected by the virus, t-Student. *p<0.05, n=3.

See FIGS. 6A, 6B and 7

The studies in fishes were carried out in ponds, where the composition of the present invention was an aqueous extract of seaweed with a reference percentage of 5% fucoidians obtained from *Macrocystes pyrifera* in combination with an extract from the *Andrographis* sp plant with a 10% of total andrographolide in a proportion of 10% and 90%, respectively, the fish feed or diet was incorporated, in a dose in the range of 0.5 to 2.5 Kh per ton of food. Preferably, at a dose of 1 kg per ton of food.

We used 450 specimens of rainbow trout (*Oncorhynchus mykiss*) with average weight of 100-120 g., however, additional fishes were available to achieve a coefficient of variation of less than or equal to 15%.

Samples of 30 fishes were taken to be analyzed in the laboratory by real-time RT-PCR technique, to discard the presence of IPNv, BKD and SRS.

An exploratory sampling was done to know the average weight of the population and to carry out the selection of the fishes chosen for the test. Only animals presenting the required weight, good condition of adaptation to the saline environment and sanitary condition approved by the veterinarian (free of IPNv, SRS and BKD) were included.

With the selection data, all animals with weight outside the selection range, as well as those with peeling or those that their condition was not appropriate for the present study, were excluded when marking.

The fishes were marked with pittags 10 days before the beginning of the test, proceeding as follows:
a) The fishes were extracted from the pond and placed in a pan with an anesthetic solution, Tricaine methanesulfonate 80%.
b) Once stage II (deep anesthesia) was reached, they were taken individually and arranged on the working table, in a lateral way, so that the head is left to the left side of the operator.
c) A needle was inserted to make the incision in flank at the level of ventral fins, through which the chip was inserted. Then he performed a small massage to slide the chip into the ventral cavity.
(d) The fishes were transferred to the basin of origin for their recovery and waiting for conformation of test ponds.

Six ponds of 1 m³ were formed from fishes previously marked with pittags. In each pond 50 fishes were deposited and of which the code of the chip was read, creating a database that associated, initial weight and length and pond number. The database allowed to follow the traceability of the tagged fishes, related to productive indexes and subsequent challenge with the pathogen. Simultaneously 2 ponds with 75 fishes each were formed, according to the same procedure, which were kept until the challenge stage, see FIG. 1.

The fishes were kept in the ponds during 10 days as acclimatization period, under controlled conditions; average temperature of 14° C. (±1° C.), salinity in a range of 31-32 ppt, oxygen 80-100% saturation and pH of 7-8. The environmental parameters were monitored daily.

During this stage, the ponds were fed with diet without the present composition, manually at 2-2.5% PC, with a 100% ration in the morning.

Daily, the unconsumed food of each pond was recovered, to later estimate the actual feeding rate of each group.

F existing mortality, it was extracted and recorded in the corresponding pond, and necropsy was carried out by trained personnel from the fish farming.

The fishes were fed 2-2.5% pc/day, during acclimatization, treatment administration and challenge stage with pathogen. The food was administered manually, delivering 100% of the ration during the morning. It should be noted that during the acclimatization and challenge a commercial diet without additives was administered.

The amount of food supplied was adjusted regularly according to the expected growth rate for the species and mortality. On a daily basis, unconsumed food was collected from the ponds, thus obtaining the actual feed intake for the estimation of subsequent productive indexes.

During the development of the test, tissue samples were taken, considering the kidney, proximal intestine and blood samples for plasma collection. The number of samples and sample time are shown in Table 3 below.

Kidney samples were taken in two 0.5 $cm^3$ pieces, which were immersed in 2 ml eppendorf tubes (individually for each fish) containing 800 μL of later RNA (Ambion). These samples were labeled and refrigerated (4-6'C) during 24 h, then cooled to −80° C.

The proximal intestine was destined to histological analysis, for which they were deposited in falcon tubes with buffered formalin. In this case, the number of samples per pond (3) was placed in the same tube, labeled with date, pond number and treatment.

Blood samples were deposited immediately after collection in eppendorf tubes prepared with heparin (25 IU). They were then centrifuged to remove the plasma, which was placed in a new tube (previously labeled) and stored in the ultra-freezer (−80° C.) until taking off them.

TABLE 5

Number and time of doing tissue sampling

| Sample Time | Blood/Plasma TK | No of sample | Kidney TK | No of sample | Proximal intestine TK | No of sample |
|---|---|---|---|---|---|---|
| T0- acclimatization begining | 1 | 3 | 1 | 3 | 1 | 3 |
|  | 2 | 3 | 2 | 3 | 2 | 3 |
|  | 3 | 3 | 3 | 3 | 3 | 3 |
|  | 4 | 3 | 4 | 3 | 4 | 3 |
|  | 5 | 3 | 5 | 3 | 5 | 3 |
|  | 6 | 3 | 6 | 3 | 6 | 3 |
| Total |  | 18 |  | 18 |  | 18 |
| T1-Treatment Ending (30 days) | 1 | 3 | 1 | 3 | 1 | 3 |
|  | 2 | 3 | 2 | 3 | 2 | 3 |
|  | 3 | 3 | 3 | 3 | 3 | 3 |
|  | 4 | 3 | 4 | 3 | 4 | 3 |
|  | 5 | 3 | 5 | 3 | s | 3 |
|  | 6 | 3 | 6 | 3 | 6 | 3 |
| Total |  | 18 |  | 18 |  | 18 |
| T2-ending challenge survivors | 1 | 10 | It is considered the testing of 5 samples per pond of the treated group and S control | | | |
|  | 2 | 10 | | | | |
|  | 3 | 10 | | | | |
| Total |  | 30 | | | | |

The food with the composition of the present invention was distributed to three ponds (triplicate), as indicated in Table 6, during 30 consecutive days. The remaining ponds (controls) continued their feeding with a standard diet throughout the evaluation period. Administration of treatment was as described above.

During this time, temperature, pH, salinity and oxygen were monitored daily. If there was mortality at this stage, it was taken out and recorded in the corresponding pond, performing an anatomopathological test.

TABLE 6

Detail administration treatment

| No Pond | No of fishes | Group | Diet Type | Time administration (days) |
|---|---|---|---|---|
| 1 | 47 | Treatment | immunostimulant | 30 |
| 2 | 47 | Control | Commercial | 30 |
| 3 | 47 | Treatment | immunostimulant | 30 |
| 4 | 47 | Control | Commercial | 30 |
| 5 | 47 | Treatment | immunostimulant | 30 |
| 6 | 47 | Control | Commercial | 30 |

Control corresponds to the commercial diet.

The immuno-modulating agent corresponds to the composition of the present invention.

Then, a challenge was performed with *P. salmonis*. Table 7 details the specifications of the *P. salmonis* isolate that was used in the inoculation of Trojan fishes.

TABLE 7

*P. salmonis* isolate specifications

| | |
|---|---|
| Laboratory of origin | ADL Diagnostic Chile Ltda. |
| Agent | *Piscirickett sia salmonis* |
| Laboratory code | PM-34152 |
| species of original isolate | Rainbow Trout |
| species where it was realized | Atlantic Salmon- Rainbow Trout |
| date original isolation | May 11, 2012 |
| Organ of isolation | Kidney |
| No of animalizations | 1 |
| Isolation condition | Reanimated cryopreserved |
| Inoculum production type | Bacterial culture |

The inoculum was administered with TCID50/ml determined by the Karber Spearman method by the laboratory ADL Diagnostic Chile Ltda. In addition, the purity of the inoculum was evaluated, considering ISAv, IPNv, BKD, *F. psycrophilum* RT-PCR analysis and bacteriological cultures in medium TSA and TSA/s at 18 and 35° of incubation.

Figure 2:
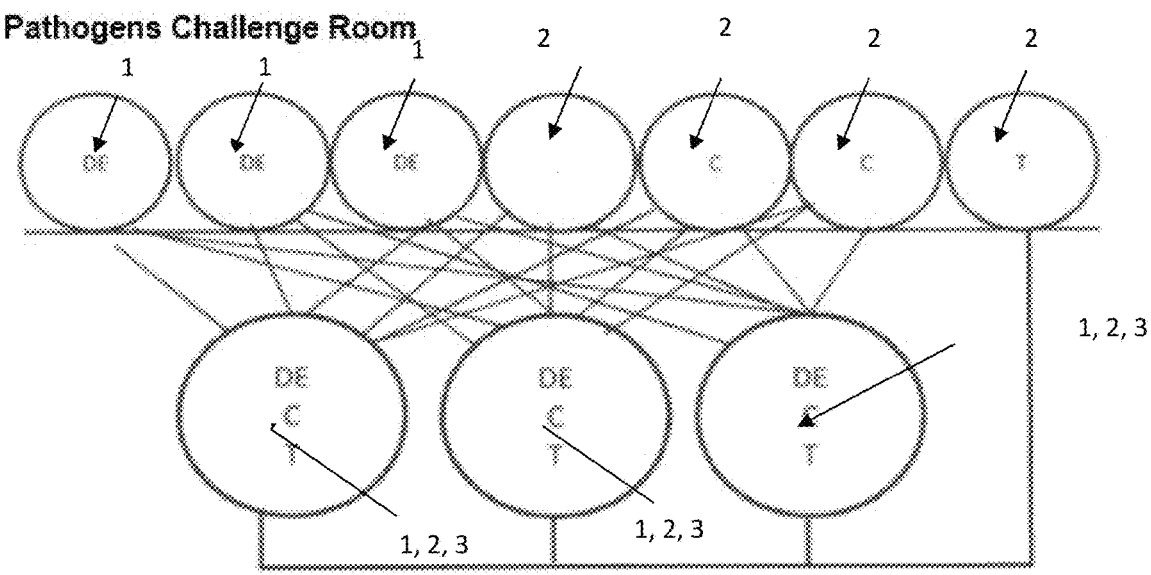
FIG. 2. It illustrates the conformation of distribution in the ponds during the challenge with *P. salmonis*, where (1) DE indicates the diet with the composition of the present invention, (2) C means the diet without the composition of the present invention and (3) T stands for trojans.

At the end of the administration of the diet with the composition of the present invention, the fishes were redistributed to perform the challenge. Three ponds of 1 $m^3$ were formed, considering the mixture of treated and untreated fishes at random in the new ponds, as indicated in table 6. At the time of the new distribution the pittag was read, assigning to each chip the group and pond, see FIG. 2.

TABLE 8

Redistribution of fishes for challenge

| No challenge pond | Origin | | | | | | |
|---|---|---|---|---|---|---|---|
| | TK-1 n = 40 Treated | TK-2 n:40 Control | TK-3 n = 40 Treated | TK-4 n = 40 Control | TK-5 n = 40 Treated | TK-6 n = 40 Control | Total |
| 7 | 13 | 14 | 13 | 13 | 14 | 13 | 80 |
| 8 | 13 | 13 | 14 | 13 | 13 | 14 | 80 |
| 9 | 14 | 13 | 13 | 14 | 13 | 13 | 80 |

Observation: The number of fishes is estimated considering mortality and sampling in the treatment administration stage, if not, the number will be adjusted to the real n.

Treated means that a diet comprising the composition of the present invention has been provided. Control means that only a commercial diet has been provided.

The challenge was achieved by cohabitation, which involved introducing fishes infected with *P. salmonis*, trojans, into healthy fishes ponds (treated and controlled), as indicated in Table 9, considering an infection pressure of 33%. The inoculum was administered intraperitoneally to the trojan group at a rate of 0.2 m/fish. The inoculation was performed according to the following procedure:

a) The fishes were extracted from the pond and placed in a container with anesthetic solution (Tricaina 80% ASL).
b) Once the anesthetic stage III was reached, they were taken individually and held with the ventral face upwards.
c) The needle was inserted at an angle of approximately 45° in the ventral midline, between the pectoral and pelvic fins, injecting 0.2 ml per fish.
d) At this stage the pittag was read by assigning to the chip code the group 'trojans', pond number and inoculation date.
e) Post application the fishes were transferred to the assigned pond, constantly monitoring the state of recovery.

TABLE 9

Distribution of challenge groups by cohabitation

| | Group | | |
|---|---|---|---|
| | TK-7 N | TK-8 n | TK-9 N |
| Treated | 40 | 40 | 40 |
| Control | 40 | 40 | 40 |
| Trojans | 40 | 40 | 40 |
| Total | 120 | 120 | 120 |

Treated means that it has received the diet with the composition of the present invention.

Control means you have only received a commercial diet.

Subsequently, the fishes were left in the ponds waiting for the appearance of mortality. During this stage, the feeding was carried out in accordance to the point 6.8 and daily environmental parameters such as temperature, salinity, oxygen and pH were registered. Mortality was identified according to the number of pittag from the database, registering daily.

The challenge lasted for 60 days, period of time that, the accumulated mortality of the control group was expected to reach 40-60%, thus ending the test.

The mortality recorded during the days of challenge was sent to the diagnostic laboratory to be analyzed by anatomopathological observations. In parallel, molecular analyzes were performed by real-time RT-PCR, for IPN and SRS viruses, to 20% of the total, considering 15 trojans, 30 of the treated group and 30 of the control group, to confirm the presence of the pathogen.

Weight and length were measured at day 0 (Beginning Acclimatization), at 30 days of treatment administration and at the end of the challenge with *P. salmonis*, on the 100% of the fish in each group. From the data, condition factor (K), feed rate (SFR), specific growth rate (SGR), % growth, thermal growth rate (GF3) and food conversion rate (FCRb).

Below are summarized in tables some of the productive variables such as average body weight, condition factor K, coefficient of variation and weight gain at the end of treatment administration. As can be seen, the final weight increased in all ponds.

TABLE 10

Body weight, condition factor, coefficient of variation and weight gain at the end of the treatment administration stage.

| | Test pond | | | | | |
|---|---|---|---|---|---|---|
| variable | N-10 Treated | N-11 Treated | N-12 Treated | N-13 Treated | N-21 Control | N-22 Treated |
| No of fishes at the begining | 47 | 47 | 47 | 47 | 47 | 47 |
| No of fishes at the ending | 47 | 47 | 46 | 47 | 47 | 46 |
| % accumulated mortality | 0 | 0 | 2.1 | 0 | 0 | 2.1 |
| Begining Weight (g) | 99.1 | 101.8 | 100.2 | 100.2 | 96.1 | 103.1 |
| Final Weight (g) | 250.2 | 254.1 | 247.4 | 249.0 | 252.0 | 243 |
| Initial condition factor (k) | 1.50 | 1.55 | 1.53 | 1.57 | 1.54 | 1.55 |
| Final condition factor (k) | 1.42 | 1.42 | 1.43 | 1.42 | 1.45 | 1.40 |
| Increases weight (g) | 151.1 | 152.3 | 147.2 | 148.8 | 155.9 | 139.9 |
| Coef. Inicial weight variation (%) | 10.6 | 12 | 9.7 | 10.1 | 10.9 | 11 |
| Coef. Final weight variation (%) | 24.1 | 21.4 | 20.7 | 19.4 | 19.8 | 20.8 |

Treated means that the diet has been supplied with the composition of the invention

TABLE 11

Food supplied, % SFR and feed conversion factor.

| | Test pound | | | | | |
|---|---|---|---|---|---|---|
| Variable | N-10 Treated | N-11 Treated | N-12 Treated | N-13 Treated | N-21 Control | N-22 Treated |
| Food supplie (kg) | 6.1 | 6.8 | 6.4 | 6.1 | 6.3 | 5.8 |
| % SFR Theorical | 2.0 | 2.0 | 2.0 | 2.0 | 2.0 | 2.0 |
| % SFR real | 1.44 | 1.57 | 1.51 | 1.44 | 1.50 | 1.37 |
| Conversion Factor (FCR,) | 0.81 | 0.89 | 0.87 | 0.82 | 0.81 | 0.83 |

Control means that only a commercial diet has been supplied.

Treated means that the diet has been supplied with the composition of the invention.

Control means that only a commercial diet has been supplied.

Table 12 summarizes the production parameters obtained during the treatment administration period (Diet with the present composition of the present invention). From the table can be seen that the growth indicators (% growth, SGR and SFR) were similar between the treated group and the control group. The data from each group did not present significant differences in weight, obtained at the end of the administration (p>0.05), in the SGR specific growth rate (p>0.05) and in the thermal growth rate GF3 (p>0.05).

TABLE 12

Summary of productive variables by treatment group

| Group | Days | Initial Weight | Final Weight | % mortality | SGR % | SFR % | FCR | GF3 | % Increase |
|---|---|---|---|---|---|---|---|---|---|
| Control | 30 | 98.83 | 249.5 | 0.7 | 1.78 | 1.48 | 0.83 | 2.33 | 152.5 |
| Treatment/ Additive | 30 | 101.17 | 249.15 | 0.7 | 1.73 | 1.46 | 0.84 | 2.227 | 145.9 |

Control means that only commercial diet has been provided.

Treatment means that a commercial diet has been provided with the composition of the present invention.

Table 13 shows the biomass increase and cumulative growth (%) post-administration of the commercial diet with the composition of the present invention. The increase in biomass fluctuated from 6.35 to 7.28 kg and the accumulated growth of 135.7 to 162.2% between the different test ponds.

The specific growth rate (SGR) ranged varied from 1.65 to 1.85 among different replicates, however, no differences were observed between the group to which a commercial diet was supplied with the composition of the present invention and the group to which only the commercial diet has been supplied. The same happened for the growth rate term (GF3), with a range of 2.16 to 2.42 behaving similarly in both groups.

TABLE 13

Biomass, percentage of relative growth, rate of thermal growth and specific rate of growth at the end of the treatment administration stage

| | Test pound | | | | | |
|---|---|---|---|---|---|---|
| Variable | N-10 Treated | N-11 treated | N-12 control | N-13 Control | N-21 control | N-22 Treated |
| Initial Biomass (kg) | 4.66 | 4.78 | 4.71 | 4.71 | 4.52 | 4.85 |
| Final Biomass (kg) | 11.8 | 11.9 | 11.4 | 11.7 | 11.8 | 11.2 |
| Biomass increases (kg) | 7.14 | 7.12 | 6.69 | 6.99 | 7.28 | 6.35 |
| "% Accumulate Increase | 152.5 | 149.6 | 146.9 | 148.5 | 162.2 | 135.7 |
| Specific Growth rate (SGR) | 1.78 | 1.76 | 1.74 | 1.75 | 1.85 | 1.65 |
| Thermal Growth rate (GF3) | 2.33 | 2.32 | 2.28 | 2.29 | 2.42 | 2.16 |

Accumulated growth is calculated from the beginning of acclimatization and at the end of treatment administration.

Control means that only a commercial diet has been provided.

Treaty means that it has been supplied a commercial diet with the composition of the present invention.

From the results obtained, T test was performed for independent samples, not observing significant differences (p>0.05) for the growth variable, between the control group and the group treated with experimental additive.

For the specific rate of thermal growth and specific rate, the same analysis was applied, not registering significant differences (p<0.05) between the treated group and the control group.

In the challenge stage with *P. salmonis*, post challenge mortality was analyzed. To do this, during the period of cohabitation the rainbow trout groups presented a similar percentage of cumulative mortality among replicates in the group of trojans.

Figure 8:
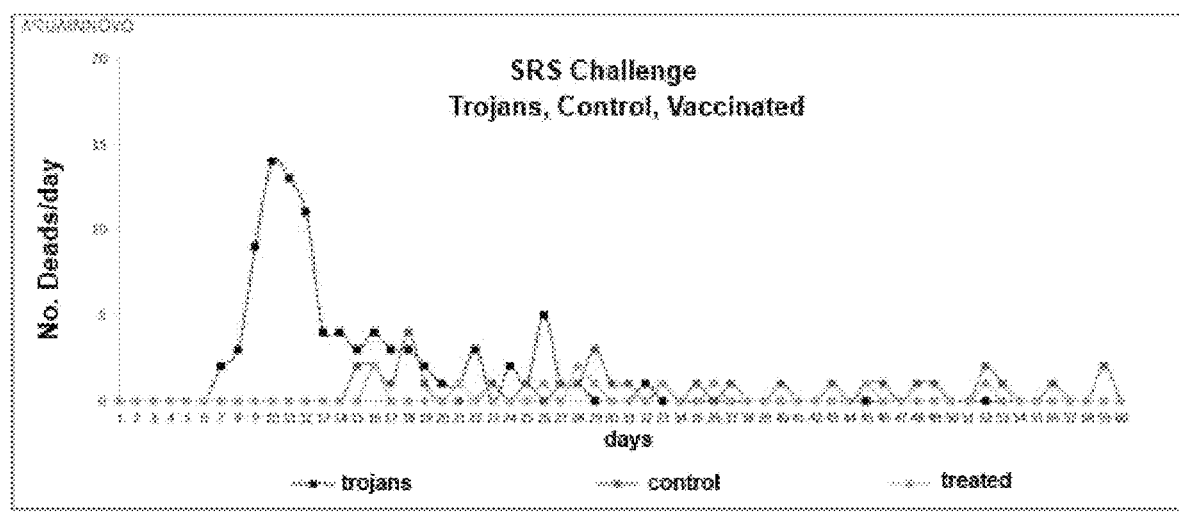
FIG. 8. It illustrates the distribution of daily mortality of the fishes from the group fed only with the diet without the composition of the present invention, the trojans and the treated, during the 60 days of study by SRS challenge.
Figure 9:
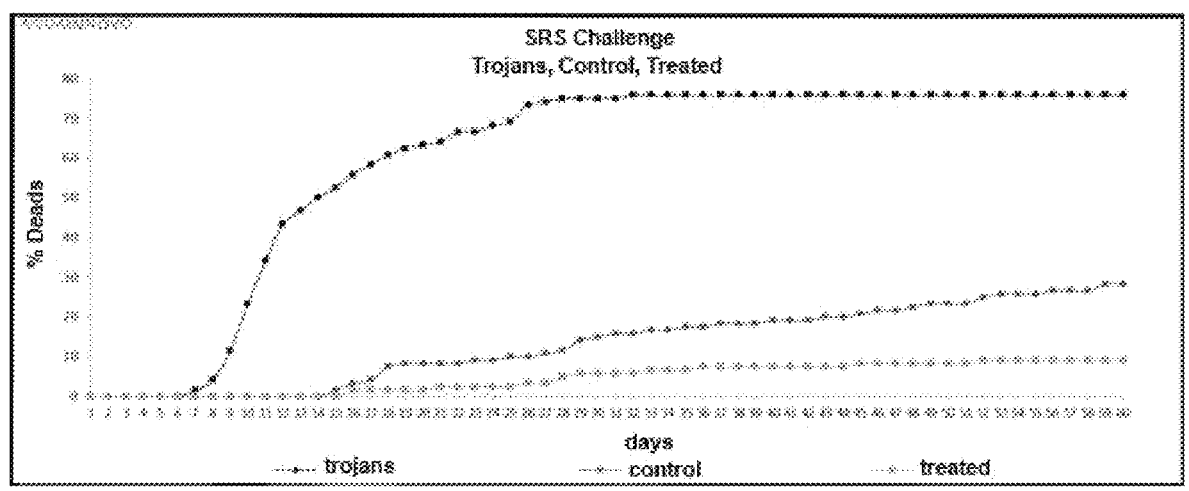
FIG. 9. It illustrates the percentage distribution accumulated of daily mortality of the fishes from the group fed with the diet only without the composition of the present invention, the trojans and the treated, during the 60 days of study by SRS challenge.

In the control group and the one administered with food of the composition of the present invention, it was higher in one of the replicates (TK C9), whereas replicate 2 and 3 (TK C10 and C11) had similar mortality, however, the trend was similar between the replicates, where the control group had higher mortality than the treated groups. FIGS. 8 and 9 show the evolution of daily and accumulated mortality per pond.

In order to confirm the reason of mortality of the challenged groups, dead fishes were analyzed by molecular techniques (RT-PCR real time) with a total of 63 samples, obtaining 100% of positive cases with presence of *P. salmonis*, and 0 positive samples for IPNV, in the different groups evaluated (see Table 14). The average Ct for the control group was 21.71 and for the experimental group 23.1.

TABLE 14

Results of the *P. salmonis* PCR analysis in rainbow trout during the cohabitation challenge

| Pond | Group | No. Analyzed | IPNV (+) | P. salmonis | Ct average of P. salmonis | % Prevalence |
|---|---|---|---|---|---|---|
| C9 | Trojan | 5 | 0 | 5 | 17.3 | 100 |
| C10 | Trojan | 5 | 0 | 5 | 23.9 | 100 |
| C11 | Trojan | 5 | 0 | 5 | 23.8 | 100 |
| C9 | Control | 10 | 0 | 10 | 23.03 | 100 |
| C10 | Control | 10 | 0 | 10 | 19.23 | 100 |
| C11 | Control | 10 | 0 | 10 | 22.87 | 100 |
| C9 | Treated | 9 | 0 | 9 | 23.48 | 100 |
| C10 | Treated | 4 | 0 | 4 | 21.38 | 100 |
| C11 | Treated | 5 | 0 | 5 | 24.66 | 100 |

Control means that only a commercial diet has been added.

Treated means that a commercial diet plus the composition of the present invention has been supplied.

In addition to molecular analysis, necropsy of the mortality was performed, external and internal lesions associated with SRS were seen. In general, the most recurrent injuries were ulcerative injuries on the skin, fin-hemorrhages, congestive intestinal serous, congestive brain, renomegaly, congestive adipose tissue, splenomegaly, and congestive pyloric blinds.

Table 15 shows the average weight, condition factor (K) and percentage of growth obtained at the end of the challenge for the control group and the treated group. As noted, the group treated with the composition of the present invention obtained higher average weight, condition factor and cumulative % growth at the end of the challenge.

TABLE 15

Average weight at the end of the challenge with *P. salmonis*

| Variable | Treated | Control |
| --- | --- | --- |
| Initial Weight (g) | 249.6 | 252.8 |
| Final Weight (g) | 567.0 | 483.8 |
| Initial condition factor (K) | 1.40 | 1.45 |
| Final condition factor (K) | 1.38 | 1.28 |
| Coef. Initial weight variation (%) | 19.4 | 22.3 |
| Coef. Final weight variation (%) | 36.9 | 43.14 |
| % accumulated growth | 127.2 | 91.3 |

Control means that only a commercial diet has been supplied.

Treated means that the commercial diet plus the composition of the present invention has been supplied.

For the interpretation of the efficacy results of the treatment, the relative percentage of survival (RPS) was calculated, based on the mortality recorded during the challenge. The RPS is the ratio between the cumulative mortality of treated fishes at the time the cumulative mortality of control (untreated) fishes reach 40-60%. The RPS is expressed according to the following formula:

RPS=1−(% mortality of fishes treated/% mortality of untreated fishes (control)·100

Also, the cumulative mortality of the control group was calculated at day 60 post challenge and at the end of the study (day 80). The RPS for the group treated by pond and as a group is presented below in Tables 16 and 17.

TABLE 16

Relative Survival Rate (RPS) in rainbow trout at 60 days post challenge

| | Control Group | | Treated |
| --- | --- | --- | --- |
| Pond | % accumulated mortality | % accumulated mortality | Group RPS(%) |
| C9 | 30 | 15 | 50.0 |
| C10 | 32.5 | 7.5 | 76.9 |
| C11 | 25 | 10 | 60.0 |
| RPS experimental product | | | 62.3 |

Control means that only a commercial diet has been supplied.

Treated means that the commercial diet plus the composition of the present invention has been supplied.

TABLE 17

Relative Survival Rate (RPS) at end-time rainbow trout

| | Control Group | Treated group | |
| --- | --- | --- | --- |
| Pound | % accumulated mortality | % accumulated Mortality | RPS (%) |
| C9 | 40 | 22.5 | 43.8 |
| C10 | 32.5 | 10 | 69.2 |
| C11 | 32.5 | 12.5 | 61.5 |
| RPS experimental product | | | 57.14 |

Control means that only a commercial diet has been added.

Treated means that a commercial diet plus the composition of the present invention has been supplied.

As seen in the tables, the RPS at day 60 was 62.3% and then decreasing to day 80 post challenge with 57.14%.

The study concluded after 133 days, having 23 days of acclimatization period, a 30 days of treatment administration period, and a 80 days cohabitation challenge. The results showed that the incorporation of the composition in the diet substantially improved the survival of the fishes when they were exposed to *Piscirickettsia salmonis* via natural infestation (cohabitation), obtaining significant differences with in relation to the group that was not treated. On the other hand, at the productive level, no differences were observed significant at the food consumption, conversion, increasing weight and specific growth rate, behaving in a similar way to a normal diet without additive.

The invention claimed is:

1. An immunostimulant composition administered to fish comprising:

an extract of *Andrographis* sp containing andrographolide and a seaweed extract containing fucoidan, wherein the ratio of andrographolide:fucoidan is in the ratio of 100:450;

wherein the seaweed extract comprises an aqueous extract of brown algae, wherein the brown algae is selected from the group consisting of *Fucus vesiculosus, Fucus evanescens, Fucus distichus, Fucus serratus, Pelvetia wrightii, Ascophyllum nodosum, Himanthalia Lorea, Bifurcaria bifurcata, Sargassum stenophyllum, Hizikia fusiforme, Durvillaea antarctica, Lessonia nigrescens, Lessonia trabeculata, Lessonia vadosa, Macrocystis pyrifera, Undaria pinnatifida, Padina pavonica, Laminarfa angustata, Laminaria japonica, Ecklonia kurome, Adenocystis utricularis, Dictyota menstrualis, Spatoglossum schroederi* and *Chordaria*; and wherein the brown algae belongs to either (1) a fucal order of algae, each member of the fucal order of algae comprising one or more binding fucose units having glycosidic bonds of type (1-3) or (1-4) and sulfated groups located at positions C-2, C-3, or C-4, or (2) a Laminare order of algae, each member of the Laminare order of algae comprising one or more binding fucose units having glycosidic bonds of type (1-2) or (1-3) and sulfated groups located at positions C-2 or C-4.

2. The composition of claim 1, wherein each member of the fucal order of algae and each member of the Laminare order of algae also comprises a galactan fraction in the bonds (1-3) and (1-6) of the sulphated groups at position C4.

3. The composition of claim 1, wherein said composition is formulated as an immunostimulant incorporated in fish food for treating infections.

4. The composition of claim 1, wherein said composition is a fish food additive having andrographolide and fucoidan.

5. The composition of claim 1, wherein the extract of *Andrographis* sp is selected from the group consisting of *Andrographis paniculata, Andrographis affinis* Nees, *Andrographis beddomei, Andrographis echioides* Nees, *Andrographis elongata, Andrographis humifusa, Andrographis lineata* Nees, *Andrographis macrobotrys* Nees, *Andrographis nallamalayana, Andrographis neesiana, Andrographis ovata, Andrographis paniculata* nees, *Andrographis rothii, Andrographis serpyllifolia, Andrographis viscosula* Nees, *Andrographis viscosula* var. *explicata* and *Andrographis wightiana*.

6. The composition of claim 1, wherein the seaweed extract is an extract of *Macrocystes pyrifera*.

7. A method for controlling and preventing infections caused by intracellular microorganisms in fishes which comprises mixing the composition of claim 1 with the fishes' food or diet.

8. The method of claim 7, comprising mixing the composition with the fishes' food or diet in a ratio in the range of 0.5 to 2.5 kg per ton of food.

9. The method of claim 8, comprising mixing the composition with the fishes' food or diet at a rate of 1 kg per ton of food.

\* \* \* \* \*

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Fwd Primer Sequence
<220> FEATURE:
<221> NAME/KEY: misc_feature
<222> LOCATION: (1)..(21)
<223> OTHER INFORMATION: Fwd Primer Sequence

<400> SEQUENCE: 1
tgggaggaga tatcacaaag c                                               21

<210> SEQ ID NO 2
```

```
<211> LENGTH: 20
<212> TYPE: DNA
<213> ORGANISM: Artificial Sequence
<220> FEATURE:
<223> OTHER INFORMATION: Rev Primer Sequence
<220> FEATURE:
<221> NAME/KEY: misc_feature
<222> LOCATION: (1)..(20)
<223> OTHER INFORMATION: Rev Primer Sequence

<400> SEQUENCE: 2
tcccaggtga cagatttcat                                           20

<210> SEQ ID NO 3
<211> LENGTH: 22
<212> TYPE: DNA
<213> ORGANISM: Artificial Sequence
<220> FEATURE:
<223> OTHER INFORMATION: Fwd Primer Sequence
<220> FEATURE:
<221> NAME/KEY: misc_feature
<222> LOCATION: (1)..(22)
<223> OTHER INFORMATION: Fwd Primer Sequence

<400> SEQUENCE: 3
ctgaatgagg tggactggta tg                                        22

<210> SEQ ID NO 4
<211> LENGTH: 17
<212> TYPE: DNA
<213> ORGANISM: Artificial Sequence
<220> FEATURE:
<223> OTHER INFORMATION: Rev Primer Sequence
<220> FEATURE:
<221> NAME/KEY: misc_feature
<222> LOCATION: (1)..(17)
<223> OTHER INFORMATION: Rev Primer Sequence

<400> SEQUENCE: 4
atcgtcctgt tcctccg                                              17

<210> SEQ ID NO 5
<211> LENGTH: 20
<212> TYPE: DNA
<213> ORGANISM: Artificial Sequence
<220> FEATURE:
<223> OTHER INFORMATION: Fwd Primer Sequence
<220> FEATURE:
<221> NAME/KEY: misc_feature
<222> LOCATION: (1)..(20)
<223> OTHER INFORMATION: Fwd Primer Sequence

<400> SEQUENCE: 5
tgcccctcca ggatgtctac                                           20

<210> SEQ ID NO 6
<211> LENGTH: 18
<212> TYPE: DNA
<213> ORGANISM: Artificial Sequence
<220> FEATURE:
<223> OTHER INFORMATION: Rev Primer Sequence
<220> FEATURE:
<221> NAME/KEY: misc_feature
<222> LOCATION: (1)..(18)
<223> OTHER INFORMATION: Rev Primer Sequence

<400> SEQUENCE: 6
cacggcccac aggtactg                                             18
```